(12) United States Patent
Wahezi

(10) Patent No.: US 12,138,454 B2
(45) Date of Patent: Nov. 12, 2024

(54) NEUROMODULATION WAVEFORM MONITORING, IDENTIFICATION AND USE NOTIFICATION

(71) Applicant: Sayed Emal Wahezi, New Rochelle, NY (US)

(72) Inventor: Sayed Emal Wahezi, New Rochelle, NY (US)

(*) Notice: Subject to any disclaimer, the term of this patent is extended or adjusted under 35 U.S.C. 154(b) by 0 days.

(21) Appl. No.: 18/438,293

(22) Filed: Feb. 9, 2024

(65) Prior Publication Data
US 2024/0325755 A1    Oct. 3, 2024

Related U.S. Application Data

(63) Continuation of application No. 18/229,743, filed on Aug. 3, 2023, now Pat. No. 11,964,153.

(60) Provisional application No. 63/456,806, filed on Apr. 3, 2023.

(51) Int. Cl.
*A61N 1/36* (2006.01)

(52) U.S. Cl.
CPC ..... *A61N 1/36071* (2013.01); *A61N 1/36132* (2013.01); *A61N 1/36135* (2013.01)

(58) Field of Classification Search
CPC ............ A61N 1/36071; A61N 1/36132; A61N 1/36135
See application file for complete search history.

(56) References Cited

U.S. PATENT DOCUMENTS

| | | |
|---|---|---|
| 7,483,747 B2 | 1/2009 | Gliner et al. |
| 7,489,966 B2 | 2/2009 | Leinders et al. |
| 8,244,360 B2 | 8/2012 | Heruth et al. |
| 8,612,018 B2 | 12/2013 | Gillbe |
| 9,492,667 B1 | 11/2016 | Kent et al. |
| 9,504,832 B2 | 11/2016 | Libbus et al. |

(Continued)

FOREIGN PATENT DOCUMENTS

WO    2023059480 A1    4/2023

OTHER PUBLICATIONS

Westbrook et al., "The Subjective Value of Cognitive Effort is Encoded by a Domain-General Valuation Network," J Neurosci, May 15, 2019; 39(20); 3934-3947.

(Continued)

*Primary Examiner* — Paula J Stice
(74) *Attorney, Agent, or Firm* — HOLLOWELL PATENT GROUP; Kelly Hollowell

(57) ABSTRACT

An exemplary neuromodulation device may be configured to treat a pain syndrome based on applying a predetermined waveform to a patient, while measuring patient physiological parameters in a feedback loop using sensors and triggering a change of the predetermined waveform to an adapted waveform, in response to detecting a change in the tolerance of the pain syndrome to the predetermined waveform. The neuromodulation device may be, for example, a Spinal Cord Stimulation Implantable Pulse Generator (SCS IPG). The SCS IPG may be configured to measure signal characteristics of an applied waveform using input electrodes while the same waveform is applied to a patient using output electrodes. The SCS IPG may compare the measured signal characteristics to signal characteristics of a predetermined waveform to determine if the applied waveform matches the predetermined waveform. The SCS IPG may send an indication to an authorization server that the predetermined waveform is in use.

16 Claims, 12 Drawing Sheets

(56) References Cited

U.S. PATENT DOCUMENTS

| | | | |
|---|---|---|---|
| 9,737,717 | B2 | 8/2017 | Moffitt et al. |
| 10,667,747 | B2 | 6/2020 | Annoni et al. |
| 11,623,092 | B2 | 4/2023 | Peyman et al. |
| 2017/0157410 | A1 | 6/2017 | Moffitt et al. |
| 2017/0304636 | A1 | 10/2017 | Steinke et al. |
| 2021/0299446 | A1 | 9/2021 | Errico et al. |
| 2022/0096822 | A1 | 3/2022 | Schepis et al. |
| 2022/0203107 | A1 | 6/2022 | Nobles et al. |
| 2023/0060761 | A1 | 3/2023 | Doan |
| 2023/0121038 | A1 | 4/2023 | John et al. |

OTHER PUBLICATIONS

"Spinal Neurostimulator Implantation," Jurisdiction E—Medicare Part B, Oct. 29, 2021.

Sivanesan, "Spinal Cord Stimulator," John Hopkins Medicine, https://www.hopkinsmedicine.org/health/treatment-testsand-therapies/pain-management.

"Spectra WaveWriter SCS System," Boston Scientific, Pain Medicine Products.

Chen et al. "Pain and Stress Detection Using Wearable Sensors and Devices—A Review," Sensors 2021, 21, 1030, https://doi.org/10.3390/s21041030, Feb. 3, 2021.

Piedade G.S. et al. "Combination of waveforms in modern spinal cord stimulation," Acta Nuerochirurgica (2022) 164:1187-1191, https://doi.org/10.1007/s00701-021-05107-4.

"Reactiv8 Implantable Neurostimulation System—P190021," Mainstay Medical Limited, https://www.fda.gov/medicaldevices/recently-approved-devices/reactiv8-im plantable-neu rosti mu lation-system-p 190021.

Prodigy, Proclaim, and Proclaim XR Spinal Cord Stimulation (SCS) Systems—P010032/S189, Abbott Medical, https://www.fda.gov/medical-devices/recently-approved-devices/prodigy-proclaim-and-proclaim-xr-spinal-cord-stimulationscs-systems-pO 10032s 189.

Proclaim Implantable Pulse Generator Clinician's Manual, Abbott Medical, 2019.

Xiong et al. "Pattern Recognition of Cognitive Load Using EEG and ECG Signals," Sensors (Basel), Sep. 2020; 20(18):5122, https://www.ncbi.nlm.nih.gov/pmc/articles/PMC7571025/.

Karri et al. Cpmarison of Spinal Cord Stimulation Waveforms for Treating Chronic Low Back Pain: Systematic Review and Meta-Analysis, Pain Phsyician 2020; 23:451-460, ISSN 1533-3159.

Eterna SCS System, Abbott Medical, https://www.neuromodulation.abbott/us/en/chronic-pain/how-neurostimulation-treats/eterna-scs-system.html.

Kardan et al. "Distinguishing cognitive effort and working memory load using scale-invariance and alpha suppression in EEG," NeuroImage, vol. 211, May 2020, 116622, https://www.sciencedirect.com/science/article/pii/S D1053811920301099?via%3Dihub.

Matheson "Detecting patients' pain levels via their brain signals," MIT News Office, Sep. 12, 2019, https://news.mit.edu/2019/detecting-pain-levels-brain-signals-0912.

Yoo et al., "Prediction of Cognitive Load from Electroencephalography Signals Using Long Short-Term Memory Network," Bioengineering 2023, 10, 361. https://doi .org/10. 3390/bioengineering 10030361.

NEUROMODULATION WAVEFORM MONITORING, IDENTIFICATION AND USE NOTIFICATION

CROSS REFERENCE TO RELATED APPLICATIONS

This application is a continuation of U.S. application Ser. No. 18/229,743, titled "Adaptive Pain Syndrome Management," now U.S. Pat. No. 11,964,153, filed by Sayed Emal Wahezi, on Aug. 3, 2023, and this application claims the benefit of U.S. Provisional Application No. 63/456,806, titled "OPEN LABEL SPINAL CORD STIMULATION IMPLANTABLE PULSE GENERATOR," filed by Sayed Emal Wahezi, on Apr. 3, 2023, and this application incorporates the entire contents of all the above-referenced applications herein by reference.

TECHNICAL FIELD

The present disclosure generally relates to the field of pain syndrome management by spinal cord stimulation (SCS) using an implantable pulse generator (IPG).

BACKGROUND

Neuromodulation refers to regulating nervous system activity through the delivery of a stimulus, such as, electrical stimulation or pharmaceutical agents directly to a target area in the body of a patient. Spinal cord stimulation (SCS) is a form of neuromodulation, involving delivery of electrical energy using one or more waveforms to the spinal cord to alter the sensation of pain. Various predetermined commercially available waveforms may be used to alter sensation of pain. One or more waveforms may be selected for use depending upon the clinical effectiveness of the waveforms to alter the sensation of pain. Altering pain sensation may be achieved through an implantable pulse generator (IPG) surgically placed under the skin and electrically connected to the spinal cord via one or more leads.

One challenge in using SCS to treat chronic pain syndromes is the potential of the pain syndrome to develop tolerance to the neuromodulation over time. Pain syndrome tolerance to neuromodulation waveforms is a phenomenon where the patient's pain syndrome becomes less responsive to one or more programmed stimulation parameters prescribed by a physician. Pain syndrome tolerance to a neuromodulation waveform may lead to a decrease in the effectiveness of the treatment. For example, the patient may not experience effective pain relief after the pain syndrome develops tolerance to a specific neuromodulation waveform.

In some cases of pain syndrome tolerance to neuromodulation, a waveform that was effective to relieve pain for a patient in the past may fail in current treatment to relieve pain. The loss of pain relief effect from one or more neuromodulation waveforms may be permanent for the patient. Even increasing the intensity of neuromodulation waveforms that previously relieved pain for the patient may fail to achieve effective pain relief if the patient's pain syndrome develops tolerance to the originally prescribed neuromodulation waveforms. Using a combination of different waveforms, frequencies, and intensities of neuromodulation may help improve pain relief and reduce the pain syndrome's development of tolerance to the neuromodulation.

Selecting and adjusting neuromodulation waveforms to improve pain relief and reduce the pain syndrome's development of tolerance to neuromodulation is a trial-and-error process. Such selection and adjustment of neuromodulation waveforms may require multiple visits to a clinic for adjustments by the physician or a clinician. Applying a different waveform recommended by the physician may require surgical explantation (removal) of an Implantable Pulse Generator (IPG) from a patient and implantation of a different IPG configured to apply SCS using another recommended waveform. This can be time-consuming and inconvenient for the patient and the clinician. The patient and physician may expend significant time and effort, and the patient may experience unnecessary pain, while trying different waveforms, frequencies, and intensities of stimulation to improve pain relief and reduce development of pain syndrome tolerance to neuromodulation waveforms. Changing IPGs is an expensive process as well; patients and insurances are burdened by the cost of replacing the device.

SUMMARY

An exemplary Open Label Spinal Cord Stimulation (SCS) Implantable Pulse Generator (IPG) may be configured to treat a pain syndrome based on applying a predetermined waveform protocol to a patient, while measuring patient physiological parameters in a feedback loop using sensors and triggering a change of the predetermined waveform protocol to an adapted waveform protocol, in response to detecting a change in the tolerance of the pain syndrome to the predetermined waveform protocol. The waveform protocol may be one or multiple waveforms cycling or alternating in patterns to prevent a pain syndrome from developing tolerance to individual waveforms. Pain syndrome tolerance may be determined based on preset, pre-implantation data. Pain syndrome tolerance to the predetermined waveform protocol may be based on the patient's pain level determined from the physiological or patient self-reported parameters. The IPG may be provisioned to apply a digitally authenticated waveform protocol during a time period governed by a digitally signed prescription.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams, or the steps (or operations) described therein without departing from the spirit of the invention. For instance, the steps may be performed in a differing order, or steps may be added, deleted, or modified. All these variations are considered to be within the scope of the claimed invention.

Like reference symbols in the various drawings indicate like elements.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Figure 1A:
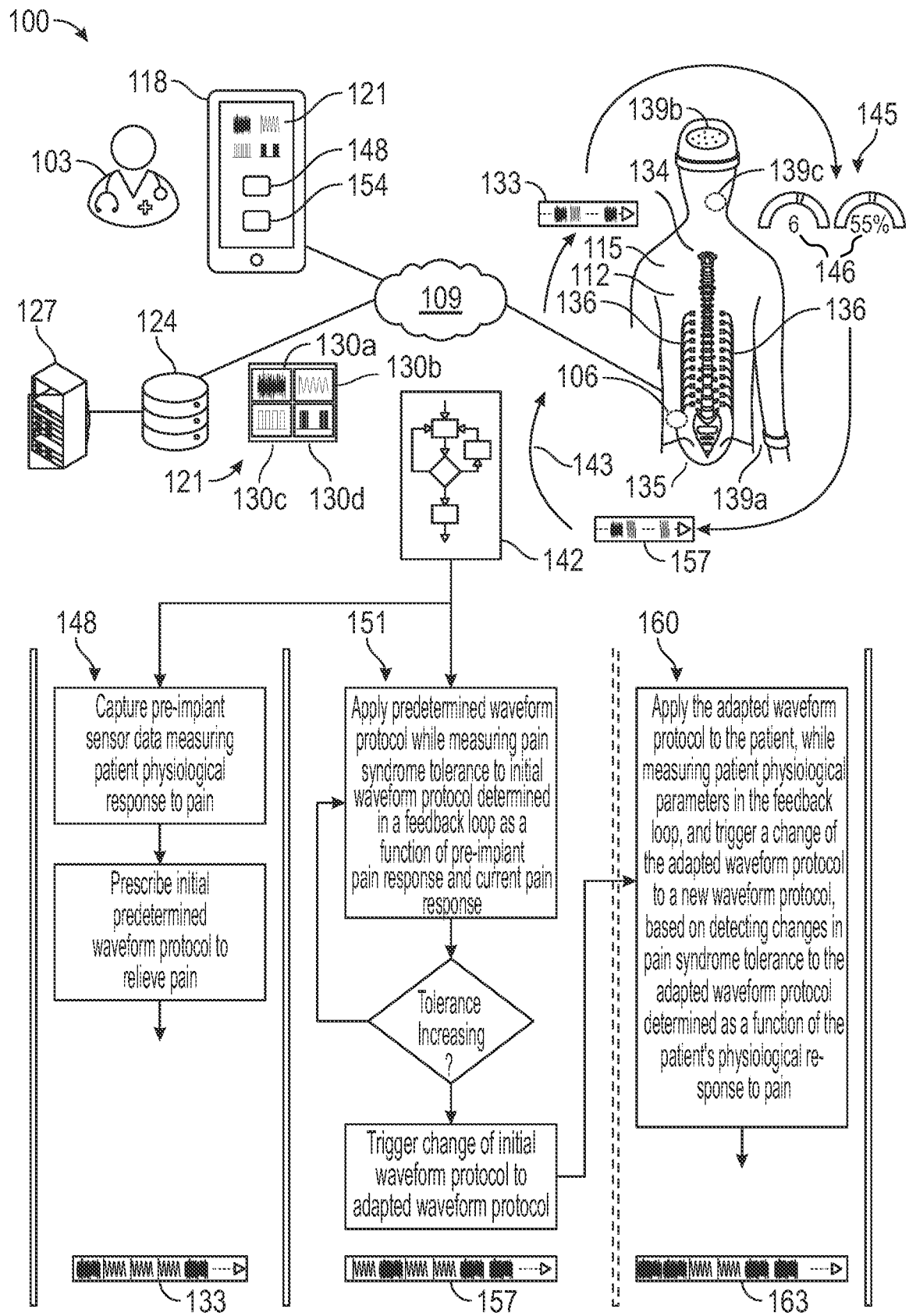
FIGS. 1A-1B depict illustrative operational scenarios wherein a doctor uses an exemplary Open Label Spinal Cord Stimulation (SCS) Implantable Pulse Generator (IPG) configured to apply a predetermined waveform protocol to a patient to treat a pain syndrome, while measuring patient physiological parameters in a feedback loop using sensors and triggering a change of the predetermined waveform protocol to an adapted waveform protocol, in response to detecting a change in the tolerance of the pain syndrome to the predetermined waveform protocol.
Figure 1B:
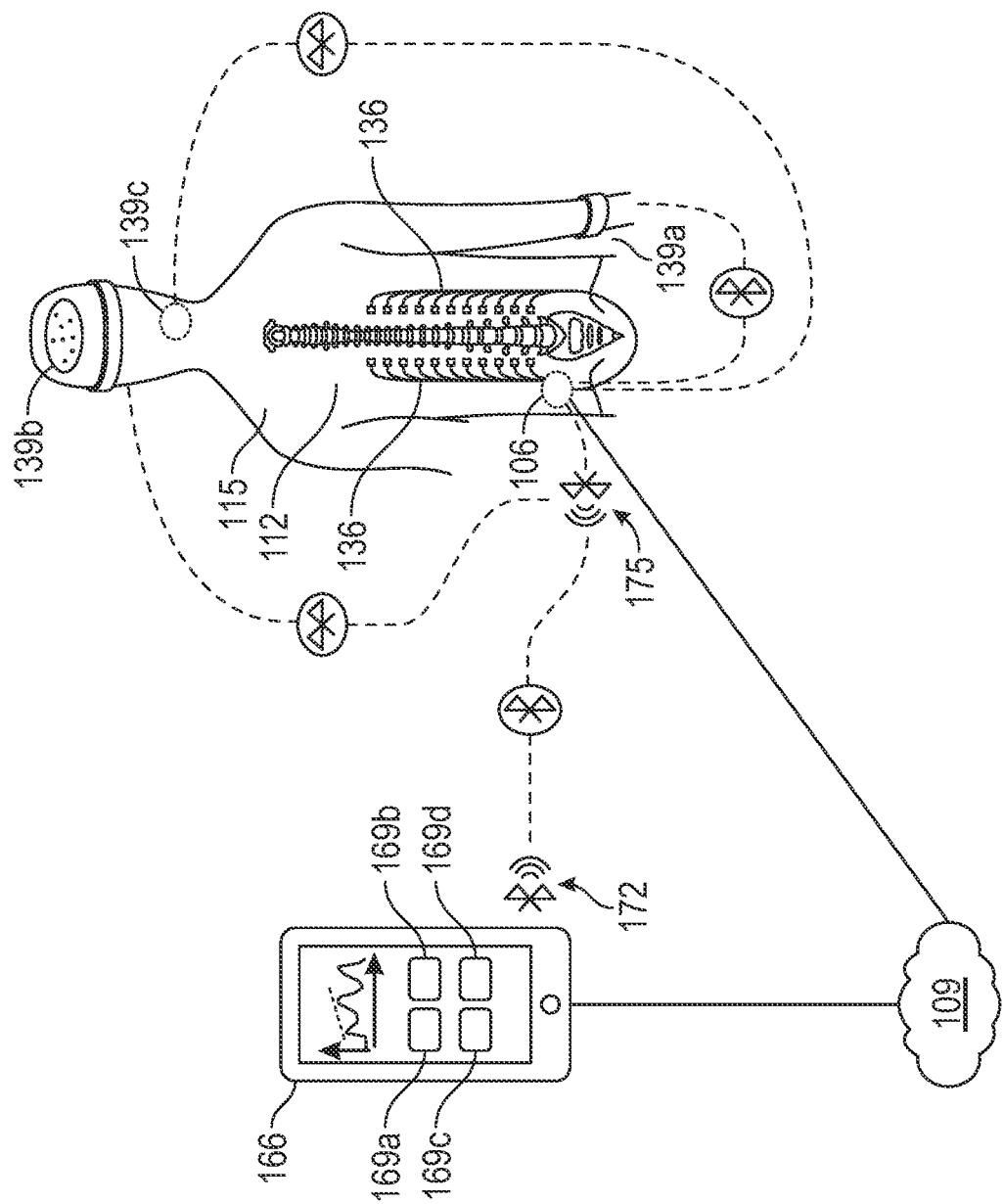

FIGS. 1A-1B depict illustrative operational scenarios wherein a doctor uses an exemplary Open Label Spinal Cord Stimulation (SCS) Implantable Pulse Generator (IPG) configured to apply a predetermined waveform protocol to a patient to treat a pain syndrome, while measuring patient physiological parameters in a feedback loop using sensors and triggering a change of the predetermined waveform protocol to an adapted waveform protocol, in response to detecting a change in the tolerance of the pain syndrome to the predetermined waveform protocol. In the exemplary neuromodulation episode 100 depicted by FIG. 1A, the doctor 103 uses the exemplary Implantable Pulse Generator (IPG) 106 via the network cloud 109 to treat the spinal cord 112 of the patient 115. In the depicted implementation the doctor 103 uses the mobile device 118 to access a library of individually available predetermined waveforms 121. The mobile device 118 is configured with an application structured to permit the doctor 103 to prescribe a selection of the individually available predetermined waveforms 121 stored in the waveform database 124. The waveform authentication and access authorization server 127 is configured to digitally authenticate each waveform of the individually available predetermined waveforms 121.

For example, the waveform authentication and access authorization server 127 is configured to digitally certify each waveform of the individually available predetermined waveforms 121 is a known waveform having specific signal characteristics. In the present disclosure a predetermined waveform or predetermined waveform protocol may be synonymous with and interchangeably referred to as a known waveform or known waveform protocol. The individually available predetermined waveforms 121 may comprise one or more licensed waveforms. The waveform authentication and access authorization server 127 is configured to authorize the IPG 106 to use any of the individually available predetermined waveforms 121 prescribed by doctor 103. The waveform authentication and access authorization server 127 may provide a digital authorization indication to the IPG 106 authorizing the IPG 106 to use one or more of the individually available predetermined waveforms 121.

For example, the digital authorization indication from the waveform authentication and access authorization server 127 to the IPG 106 may authorize the IPG 106 to download and use one or more of the individually available predetermined waveforms 121 prescribed by the doctor 103 to treat the patient 115. The IPG 106 may be configured by the doctor 103 to use one or more of the individually available predetermined waveforms 121 for a period of time governed by a digital prescription digitally signed by the doctor. In another example, the IPG 106 may be configured to apply one or more waveforms prescribed by the doctor 103 until a prescription expiration time. The IPG 106 may revert from applying a prescribed waveform to applying a default waveform or default combination of waveforms when a prescription expires.

In the depicted implementation, the individually available predetermined waveforms 121 stored in the waveform database 124 comprise the exemplary licensed waveforms 130a, 130b, 130c and 130d. In the depicted implementation the waveforms 130a, 130b, 130c and 130d are non-limiting illustrative example waveforms. The individually available predetermined waveforms 121 stored in the waveform database 124 may comprise any waveform. In the depicted implementation, the doctor 103 prescribes the initial predetermined waveform protocol 133 to relieve patient 115 pain. In the depicted implementation, the initial predetermined waveform protocol 133 comprises the individual licensed waveform 130a and the individual licensed waveform 130b. The mobile device 118 configures the IPG 106 to download the prescribed predetermined waveform protocol 133. The IPG 106 is configured to use the initial predetermined waveform protocol 133 to energize the electrodes 136 for treating the patient 115 spinal cord 112.

In the depicted implementation, the IPG 106 applies the initial predetermined waveform protocol 133 based on cycling or alternating the individual licensed waveform 130a and the individual licensed waveform 130b in a pattern specifically prescribed in a user interface by the doctor 103. In the depicted scenario the patient 115 has a pain syndrome 134 comprising one or more condition causing pain. The patient 115 pain syndrome 134 may develop tolerance 135 to one or more waveform over time. In an illustrative example, patient 115 may not experience effective pain relief after the pain syndrome 134 develops tolerance 135 to a waveform. Pain syndrome 134 tolerance 135 to the predetermined waveform protocol 133 may increase with time, causing the patient 115 to experience increasing pain as the waveform protocol 133 effectiveness declines. The specific cycling or alternating pattern prescribed may be prescribed by the doctor 103 to relieve the patient 115 pain while preventing the patient 115 pain syndrome 134 from developing tolerance 135 to an individual waveform or a predetermined waveform protocol. The IPG 106 may be configured to download and run predetermined waveforms in algorithmically determined waveform protocols. The IPG 106 may run the predetermined waveforms individually or in combination, and/or in series or parallel.

In the depicted implementation, the IPG 106 is configured to measure patient 115 physiological parameters 146 based on sensor data 145 in the feedback loop 143 and trigger a modification of the predetermined waveform protocol 133 to an adapted waveform protocol 157, based on tolerance 135 of the pain syndrome 134 to the predetermined waveform protocol 133. In the depicted implementation, tolerance 135 of the pain syndrome 134 to the predetermined waveform protocol 133 is determined in the feedback loop 143 as a function of the physiological parameters. The depicted IPG 106 is configured to determine the patient 115 physiological parameters based on sensor data.

For example, the IPG 106 is configured to receive heart rate (HR), heart rate variability (HRV), RR Interval (RR) and body temperature measurements from sensors 139 configured in wrist band 139a. The IPG 106 is configured to measure changes in brain activity (for example to monitor REM sleep) using the hat 139b configured with EEG sensors and the vagal and hypoglossal sleep sensor/stimulator 139c. The IPG 106 may be configured with sensors 139 (for example an accelerometer or magnetometer) measuring parameters related to physical activity (for example resting or walking) or body position (for example lying down sitting).

The IPG 106 may also be configured to autonomously change waveforms or sequences of waveforms based on measuring specific changes in patient physiology based on the sensor data 145. The IPG 106 may be configured to autonomously change waveforms or waveform signal characteristics, such as for example, waveform frequency, amplitude, power or duty cycle depending on physiologic parameters 146 that indicate increased pain. The IPG 106 may physiologically interact bidirectionally with the patient 115. For example, the IPG 106 may be configured to receive information from the sensors 139 to change spinal cord activity and deliver information to the EEG and sleep sensors to alter sleep and provide extracranial therapy. In the depicted implementation, the IPG 106 is configured with the waveform protocol prescription engine (WPPE) 142. In the illustrated implementation the WPPE 142 applies the predetermined waveform protocol 133 to the patient 115, while measuring the physiological response of the patient 115 to pain based on the sensor data 145. In the depicted implementation, the WPPE 142 may detect a change in the patient 115 physiological response to pain while measuring patient 115 physiological parameters 145 in the feedback loop 143. In the depicted implementation the WPPE 142 may determine the detected change in the patient 115 physiological response to pain indicates the efficacy of the predetermined waveform protocol 133 to relieve pain has decreased as result of increased patient 115 pain syndrome 134 tolerance 135 to the predetermined waveform protocol 133. In another illustrative example, the WPPE 142 may determine the patient 115 pain syndrome 134 tolerance 135 has increased relative to preset, pre-implantation patient 115 physiological data. The pre-implantation patient 115 physiological data may be captured during the neuromodulation trial procedure 148 initiated by the doctor 103 using the trial 148 button configured in the mobile device 118.

During the exemplary neuromodulation trial procedure 148 the IPG 106 may be configured to capture pre-implant sensor data measuring the patient 115 physiological response to pain while applying one or more prescribed waveform to the patient 115 as a baseline or reference pain response for the patient 115. The doctor 103 may prescribe the initial predetermined waveform protocol 133 to relieve pain for the patient 115, based on the neuromodulation trial procedure 148. The reference pain response for the patient 115 measured using the pre-implant sensor data correlates with the initial efficacy of the prescribed waveform applied while the reference pain response was captured. In an illustrative example the IPG 106 may be configured with the pre-implantation patient 115 physiological data corresponding to the baseline or reference physiological response to pain for the patient 115.

In the depicted implementation, the doctor 103 may initiate the neuromodulation treatment 151 procedure using the treat 154 button configured in the mobile device 118. During the exemplary neuromodulation treatment procedure 151 the WPPE 142 applies the predetermined waveform protocol 133 while measuring patient 115 pain syndrome 134 tolerance 135 to the waveform determined as a function of pre-implant reference pain response and current pain response. In a feedback loop the WPPE 142 performs a test to determine if the patient 115 pain syndrome 134 tolerance 135 to the predetermined waveform protocol 133 has increased (that is, a decrease in efficacy of the prescribed waveform 133 to relieve pain in the patient 115) corresponding with an increase in the patient 115 physiological response to pain measured using the sensor data 145. In the depicted example the increased patient 115 pain syndrome 134 tolerance 135 to the predetermined waveform protocol 133 triggers WPPE 142 to change the predetermined waveform protocol 133 to the adapted waveform protocol 157. In the depicted implementation, the WPPE 142 continues long term neuromodulation treatment 160 applying the adapted waveform protocol 157 to the patient 115 while measuring patient physiological parameters 146 in the feedback loop 143. The WPPE 142 triggers a change of the adapted waveform protocol 157 to the modified treatment waveform protocol 163 based on changing patient 115 pain syndrome 134 tolerance 135 to the adapted waveform protocol 157 determined as a function of the patient 115 physiological response to pain measured using the sensor data 145.

In FIG. 1B, is a schematic illustration of sensors and effectors 139a,b,c configured for bidirectional information flow with the SCS IPG 106 to change spinal cord 112 activity with the effectors 139 and mitigate a pain crisis based on adjusting the stimulation form the effector in response to sensor information indicating the pain crisis. The method may further comprise: receiving sensor information 145 comprising the physiological response of the patient 115 to pain from at least one sensor, using the SCS IPG 106 processor 200; comparing the received sensor information 145 from at least one sensor to reference sensor information comprising the physiological response of the patient 115 captured when the patient 115 was not experiencing a pain crisis, to determine if the patient is experiencing a pain crisis based on the comparison, using the SCS IPG 106 processor 200; in response to determining the patient 115 is experiencing a pain crisis, activating at least one effector 139 configured to change spinal cord 112 activity based on providing external stimulation to the patient 115, using the SCS IPG 106 processor 200; and adjusting the external stimulation to the patient 115 to mitigate the pain crisis, using the SCS IPG 106 processor 200.

In one embodiment, the SCS IPG 106 has a direct connection to the spinal cord 112 with an IPG capable of pairing with different sensors. In one embodiment, a wristband 139a, digital EEG hat 139b and/or vagal stimulator 139c may be communicatively paired with the SCS IPG 106 and a mobile device 166 using the BLUETOOTH links 172 and 175. The mobile device 166 may be configured with a mobile app designed to monitor patient physiological parameters such as, for example, blood pressure, oxygen tension, heart rate and RR interval. For example the patient's measured blood pressure, oxygen tension, heart rate and RR interval may be presented to the patient using displays 169a,b,c,d configured in the mobile app hosted by the mobile device 166. The SCS IPG 106 or the mobile device 166 may correlate an increase in heart rate with a change in oxygen tension measured by the sensors. This detected change in pain response may be detected and recorded by the SCS IPG 106 or the mobile device 166 based on sensor data received from the wristband device and/or other sensors. In an illustrative example, the SCS IPG 106 or the mobile device 166 may be configured to provide a response to the change in pain response such as but not limited to an acupressure treatment using the wristband device and/or music or other content triggered in the mobile app to calm the patient. This wrist wearable device may also be used as a monitoring device to record moment-to-moment changes such as when a patient becomes very anxious in response to pain or PTSD. The wrist wearable device may also provide biofeedback. as a type of cognitive behavioral therapy whereby a patient can see their heart rate and their oxygen tension and other physiological parameters on the mobile app screen. In one embodiment, a sensor device may not be wearable, but may be external to the IPG and configured as the vagal nerve stimulator 139c. In this embodiment, the devices may interface with all of these other devices, and the vagal nerve stimulator.

Figure 2:
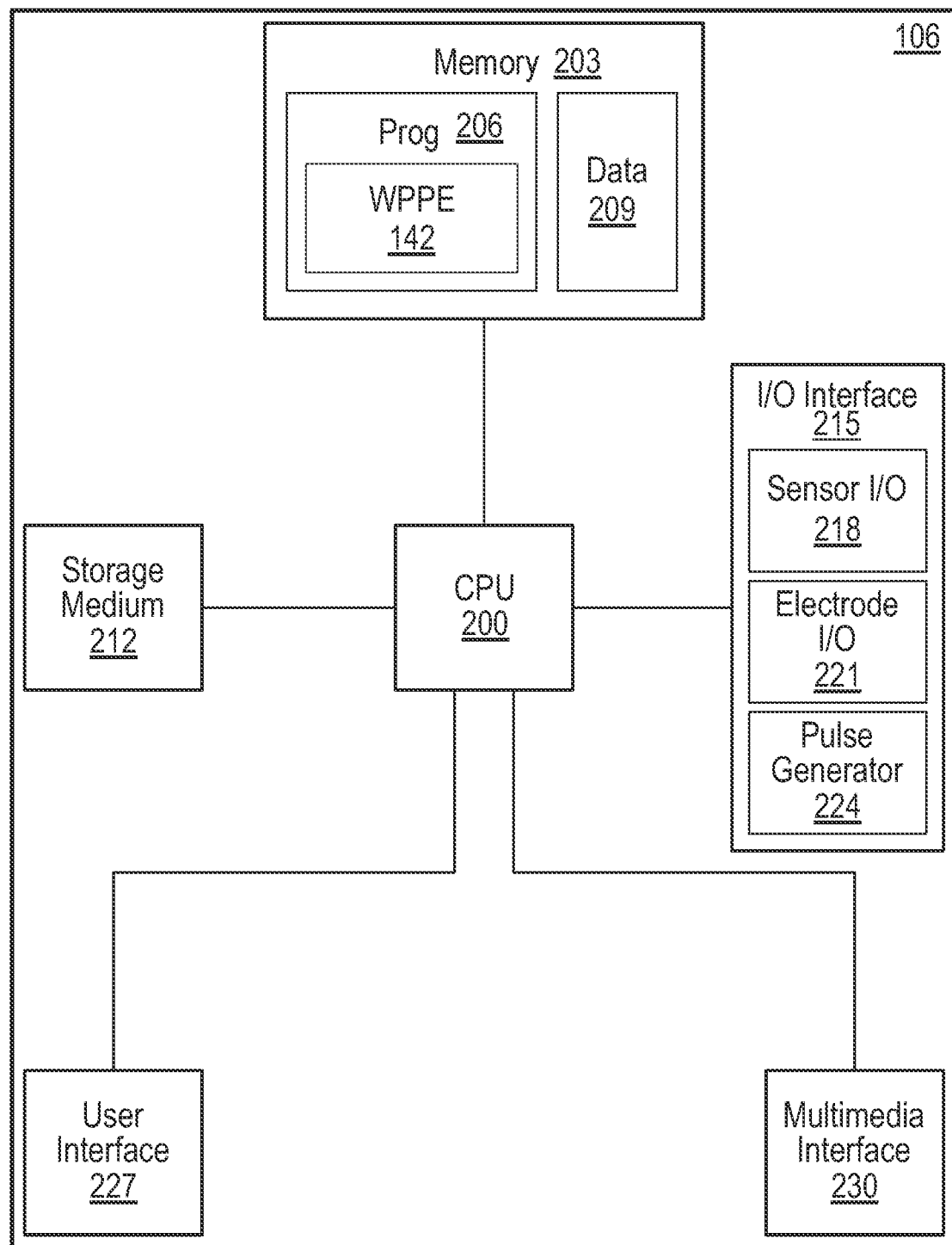
FIG. 2 depicts a block diagram of an exemplary Open Label SCS IPG hosting an exemplary waveform protocol prescription engine (WPPE) configured to apply a predetermined waveform protocol to a patient to treat a pain syndrome, while measuring patient physiological parameters in a feedback loop using sensors and trigger a change of the predetermined waveform protocol to an adapted waveform protocol, in response to detecting a change in the tolerance of the pain syndrome to the predetermined waveform protocol.

FIG. 2 depicts a block diagram of an exemplary Open Label SCS IPG hosting an exemplary waveform protocol prescription engine (WPPE) configured to apply a predetermined waveform protocol to a patient to treat a pain syndrome, while measuring patient physiological parameters in a feedback loop using sensors and trigger a change of the predetermined waveform protocol to an adapted waveform protocol, in response to detecting a change in the tolerance of the pain syndrome to the predetermined waveform protocol. In FIG. 2, the block diagram of the exemplary SCS IPG 106 includes the CPU (processor) 200 and the memory 203. In the depicted implementation, the processor 200 is in electrical communication with the memory 203. The processor 200 may be operably coupled with one or more memory 203 via a communication network. In the depicted implementation the memory 203 includes the program memory 206 and the data memory 209. The depicted program memory 206 includes processor-executable program instructions implementing WPPE 142. In some embodiments, the illustrated program memory 206 may include processor-executable program instructions configured to implement an OS (Operating System). In various embodiments, the OS may include processor executable program instructions configured to implement various operations when executed by the processor 200. In some embodiments, the OS may be omitted. In some embodiments, the illustrated program memory 206 may include processor-executable program instructions configured to implement various Application Software. In various embodiments, the Application Software may include processor executable program instructions configured to implement various operations when executed by the processor 200. In some embodiments, the Application Software may be omitted. In the depicted embodiment, the processor 200 is communicatively and operably coupled with the storage medium 212. The storage medium 212 may be configured to implement various data storage and data retrieval operations for the processor 200 such as for example, read/write, read/only or non-volatile storage and retrieval. In the depicted embodiment, the processor 200 is communicatively and operably coupled with the I/O (Input/Output) interface 215. In the depicted embodiment, the I/O interface 215 includes a network interface. In various implementations, the network interface may be a wireless network interface. In some designs, the network interface may be a Wi-Fi interface. In some embodiments, the network interface may be a BLUETOOTH interface. In an illustrative example, the SCS IPG 106 may include more than one network interface. In some designs, the network interface may be a wireline interface. In some designs, the network interface may be omitted. In the depicted implementation the I/O interface 215 includes the sensor I/O interface 218. The sensor I/O interface 218 may be configured to receive sensor information from one or more sensor configured to measure one or more physiological parameters. The sensor information may be received by the I/O interface 218 using one or more wired or wireless interface. The sensor I/O interface 218 may be configured to send information to one or more effector configured to provide physical stimulation to a patient. The information sent to the one or more effectors from the I/O interface 218 may control one or more parameter of the stimulation for example, the rate, intensity, frequency or time period of the physical stimulation provided by the one or more effector.

In the depicted implementation, the processor 200 is operably coupled with the sensor I/O interface 218. In the depicted implementation the I/O interface 215 includes the electrode I/O interface 221. The electrode I/O interface 221 may be configured to energize one or more electrode operably coupled with the electrode I/O interface 221. The one or more electrodes may be grouped into one or more sets of individual electrodes which may be energized with the same and/or distinct and separate waveforms at the same time as configured by the processor 200.

The electrode I/O interface 221 may be configured to receive input energy form one or more electrodes operably coupled with the I/O interface 221. The input energy from the one or more electrodes may be used by the processor 200 to measure energy applied with the SCS IPG 106 by one or more waveform. In the depicted implementation, the processor 200 is operably coupled with the electrode I/O interface 221. In the depicted implementation the I/O interface 215 includes the pulse generator 224. The pulse generator 224 may be configured to generate any arbitrary waveform to be applied using the electrode I/O interface 221. In the depicted implementation, the processor 200 is operably coupled with the pulse generator 224. In the depicted embodiment, the processor 200 is communicatively and operably coupled with the user interface 227.

In various implementations, the user interface 227 may be adapted to receive input from a user or send output to a user. In some embodiments, the user interface 227 may be adapted to an input-only or output-only user interface mode. In various implementations, the user interface 227 may include an imaging display. In some embodiments, the user interface 227 may include an audio interface. In some designs, the audio interface may include an audio input. In various designs, the audio interface may include an audio output. In some implementations, the user interface 227 may be touch-sensitive. The user interface 227 may be configured to permit graphical waveform or signal input drawn using a stylus or a user's finger, in contact with a touch-sensitive surface. In some designs, the SCS IPG 106 may include an accelerometer operably coupled with the processor 200. In various embodiments, the SCS IPG 106 may include a GPS module operably coupled with the processor 200. In an illustrative example, the SCS IPG 106 may include a magnetometer operably coupled with the processor 200. In some embodiments, the user interface 227 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include electrical signal sensing subsystems or modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In various implementations, the depicted memory 203 may contain processor executable program instruction modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In some embodiments, the input sensor array may include audio sensing subsystems or modules configurable by the processor 200 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 203 may contain processor executable program instruction modules configurable by the processor 200 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 200 is communicatively and operably coupled with the multimedia interface 230. In the illustrated embodiment, the multimedia interface 230 includes interfaces adapted to input and output of audio, video, and image data. In some embodiments, the multimedia interface 230 may include one or more still image camera or video camera. In various designs, the multimedia interface 230 may include one or more microphone. In some implementations, the multimedia interface 230 may include a wireless communication means configured to operably and communicatively couple the multimedia interface 230 with a multimedia data source or sink external to the SCS IPG 106. In various designs, the multimedia interface 230 may include interfaces adapted to send, receive, or process encoded audio or video. In various embodiments, the multimedia interface 230 may include one or more video, image, or audio encoder. In various designs, the multimedia interface 230 may include one or more video, image, or audio decoder. In various implementations, the multimedia interface 230 may include interfaces adapted to send, receive, or process one or more multimedia stream. In various implementations, the multimedia interface 230 may include a GPU. In some embodiments, the multimedia interface 230 may be omitted. The multimedia interface 230 may be implemented in a mobile device operably coupled with the processor 200. For example, the multimedia interface 230 may be configured in the doctor 103 mobile device 118 depicted at least by FIG. 1A. The multimedia interface 230 may be configured in the patient 115 mobile device 166 depicted at least by FIG. 1B. Useful examples of the illustrated SCS IPG 106 include, but are not limited to, personal computers, servers, tablet PCs, smartphones, or other computing devices. In some embodiments, multiple SCS IPG 106 devices may be operably linked to form a computer network in a manner as to distribute and share one or more resources, such as clustered computing devices and server banks/farms. In some embodiments, an exemplary SCS IPG 106 design may be realized in a distributed implementation. An SCS IPG 106 design may be partitioned between a client device, such as, for example, a phone, and, a more powerful server system with greater resources, such as for example, computation, memory or storage capacity. In various designs, a SCS IPG 106 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary SCS IPG 106 may be configured to operate on a device with less processing power, such as, for example, various gaming consoles, which may not have sufficient processor power, or a suitable CPU architecture, to adequately support SCS IPG 106. Various embodiment designs configured to operate on a such a device with reduced processor power may work in conjunction with a more powerful server system.

FIGS. 3A-3F together depict various views of exemplary waveform protocol configuration, editing and prescribing graphical user interfaces. The SCS IPG 106 processor 200 may configure the pulse generator 224 (depicted at least by FIG. 2) to energize electrodes 136 (depicted at least by FIG. 1A) with one or more waveform configured or selected using interfaces such as depicted by any of FIGS. 3A-3F.

Figure 3A:
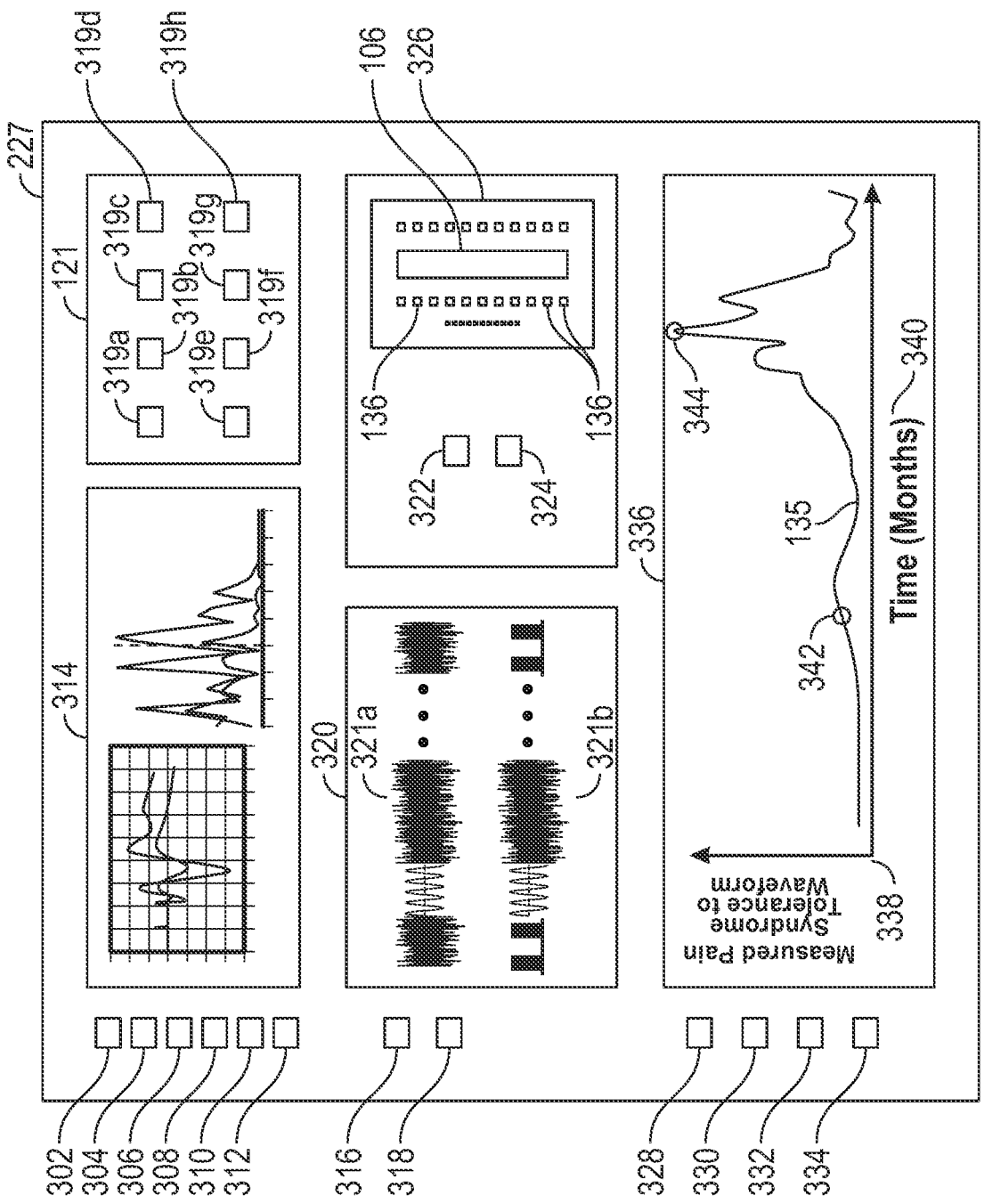
FIGS. 3A-3F together depict various views of exemplary waveform protocol configuration and prescribing graphical user interfaces.

FIG. 3A shows the exemplary user interface 227 configured for waveform and waveform protocol customization, configuration and prescribing. The exemplary graphical waveform customization interface 314 provides the configuration buttons 302, 304, 306, 308, 310, and 312 permitting a user to modify or configure respective waveform parameters such as, frequency, amplitude, running time, waveform selection, prescription expiration time, and duty cycle. The waveform parameters modified or configured by the depicted configuration buttons may be programmed by the SCS IPG 106 processor 200.

In FIG. 3A, the waveform selection buttons 319*a,b,c,d, e,f,g,h* are configured to select individual waveforms or waveform protocols from the waveform library 121 for application by the SCS IPG 106. In the implementation implemented by FIG. 3A the waveform protocol selection and configuration interface 320 is configured to permit a user to customize waveform protocols formed from individual waveforms selected from the waveform library 121. In the depicted implementation, the exemplary waveform protocols 321*a* and 321*b* have been customized from individual waveforms and stored in the SCS IPG 106. The SCS IPG 106 may be configured to apply the waveform protocols 321*a* and 321*b* using the custom waveform protocol selection buttons 316 and 318. For example, the waveform protocol selection and configuration interface 320 may be configured to retrieve individual waveforms from the waveform library 121. The individual waveforms or waveform protocols to be retrieved from the waveform library 121 may be selected for customization or configuration in a waveform protocol using the waveform selection buttons 319*a,b,c,d, e,f,g,h*. The selected waveforms may be arranged by clicking, dragging and dropping the selected waveforms in the waveform protocol selection and configuration interface 320 to compose a customized waveform protocol. For example, a waveform protocol may be formed from individual waveforms based on dragging/dropping individual waveforms into a particular pattern to form a cycling sequence of alternating distinct waveforms in the protocol selection and configuration interface 320. In an illustrative example each individual waveform in a customized waveform protocol may be configured with an on time and off time, a start time in the sequence, an end time in the sequence, and an ordinal position in the sequence, using the waveform protocol selection and configuration interface 320.

In FIG. 3A, the exemplary electrode input/output (I/O) programming interface 326 is configured to permit programming individual electrodes as input or output and assign particular waveforms and/or waveform protocols to particular output electrodes. In the depicted implementation the electrode I/O programming interface 326 may be configured to operate in conjunction with the waveform protocol selection and configuration interface 320 to permit assigning waveforms and/or waveform protocols to individual electrodes. For example the user may tap or click one or more electrode 136 displayed in the electrode I/O programming interface 326 to select multiple electrodes. In the depicted implementation the output activator 322 assigns selected electrodes to an output set to be energized with one or more waveform. In the depicted implementation the input activator 324 assigns selected electrodes to an input set for measuring received energy from one or more waveform applied to the patient. The user may select a waveform or waveform protocol in the waveform protocol selection and configuration interface 320 and assign the selected waveform or waveform protocol to the selected or grouped electrodes. In an illustrative example the SCS IPG 106 processor 200 may configure the pulse generator 224 to energize the selected or grouped electrodes with the assigned waveforms or waveform protocols. An exemplary physical IPG electrode I/O interface configurable using the electrode I/O programming interface 326 is described with reference to FIG. 11.

In FIG. 3A, the exemplary pain syndrome tolerance graphical user interface 336 is configured to present the measured pain syndrome tolerance 135 as a function of time 340. In the depicted implementation the measured pain syndrome tolerance 135 position on the dependent axis 338 represents the change in the tolerance 135 of a patient 115 pain syndrome 134 to a particular waveform or waveform protocol over time. The tolerance 135 of a patient 115 pain syndrome 134 to a particular waveform or waveform protocol at the particular time may be determined as a function of pre-implant trial phase data comprising patient 115 physiological response to pain and the patient 115 current physiological response to pain in a subsequent treatment phase. The SCS IPG 106 processor 200 may compare the pre-implant trial phase patient 115 physiological response to pain and the patient 115 current physiological response to pain to determine the tolerance 135 of the pain syndrome 134 to the particular waveform. The patient physiological response to pain is based on data from sensors configured to measure patient physiological parameters such as for example, heart rate, blood pressure, RR interval, brain waves (EEG), or oxygen tension, in the trial phase and a subsequent treatment phase. For example, the tolerance 135 of the pain syndrome 134 to a particular waveform or waveform protocol may correlate with the pain relief effect of the particular waveform or waveform protocol measured in the trial phase. In the depicted pain syndrome tolerance graphical user interface 336 the measured pain syndrome tolerance 135 as a function of time 340 is a difference between the patient physiological response to pain for a particular waveform measured in the trial phase and the current patient physiological response to pain measured during a subsequent treatment phase by the SCS IPG 106 processor 200 in the feedback loop 143. In the depicted implementation, the reference tolerance 342 is the tolerance 135 of the pain syndrome 134 established in the trial phase for the particular waveform or waveform protocol. In the depicted implementation the trigger tolerance 344 is a threshold tolerance trigger value set by the doctor 103 to trigger a change of the predetermined waveform protocol 133 to an adapted waveform protocol 157, in response to detecting the tolerance 135 of the pain syndrome 134 to the predetermined waveform protocol 133 reached the trigger point 344.

Figures 3B, 3C:
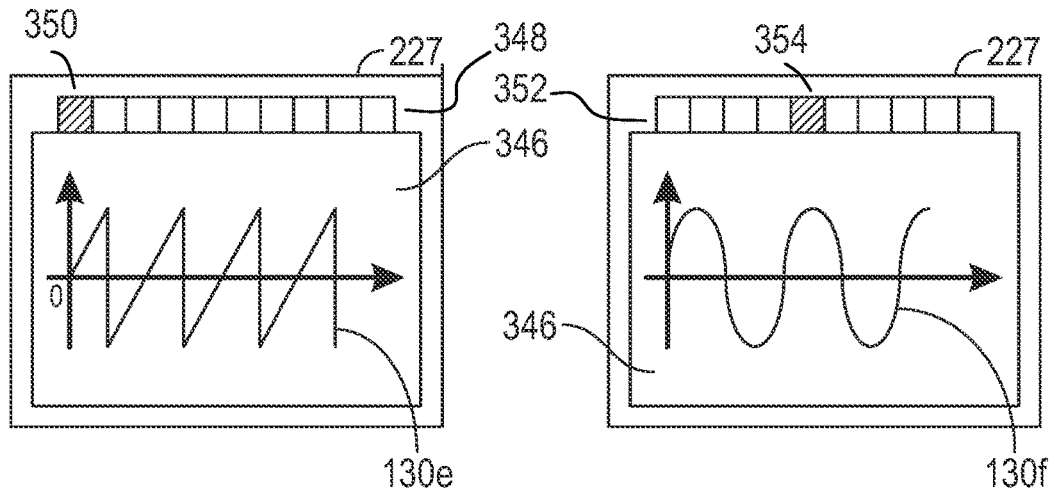
Figures 3D, 3E:
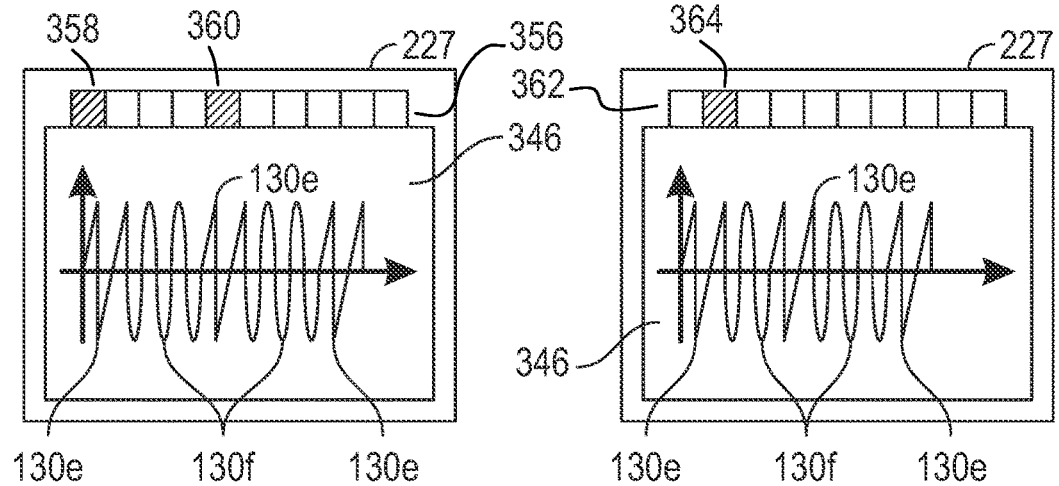
Figure 3F:
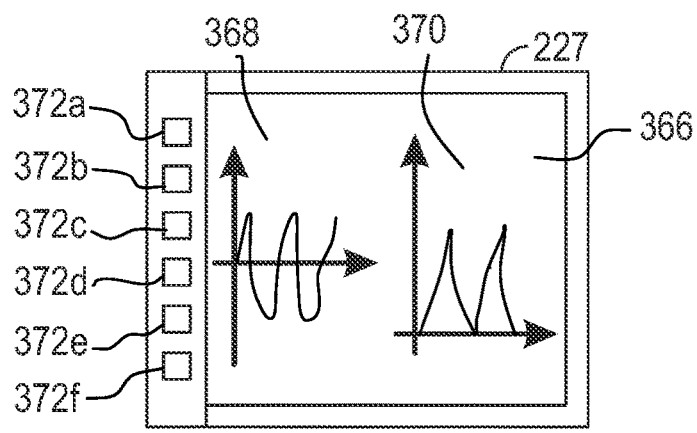

FIGS. 3B-3E are exemplary waveform configuration and selection interfaces. The waveform configuration and selection interface 346 includes the row of waveform selection tabs 348. In FIG. 3B the exemplary waveform 130e has been selected by tab 350 for application by the SCS IPG 106. In FIG. 3C the exemplary waveform 130e has been selected by tab 354 for application by the SCS IPG 106. In FIG. 3D the exemplary waveform 130e and waveform 130f have been selected by tabs 358 and 360 respectively, from the row of waveform selection tabs 356. In FIG. 3D the exemplary waveform 130e and waveform 130f have been configured in an exemplary customized waveform protocol comprising two waveforms. selected by tabs 358 and 360 respectively, from the row of waveform selection tabs 356. In FIG. 3E the exemplary waveform protocol configured in FIG. 3D has been stored in the SCS IPG 106 for section with the custom waveform protocol section tab 364 in the row of tabs 362. FIG. 3F shows a waveform customization and editing interface configured to permit a user to create and modify existing and new waveforms. In FIG. 3F the waveform customization and editing interface 356 is configured for customizing and editing the waveforms 368 and 370. The configuration buttons 372a, 372b, and 372c permit a user to modify parameters of the waveform 368 such as, frequency, amplitude, running time, prescription, expiration time, and duty cycle respectively. The configuration buttons 372d, 372e, and 372f permit a user to modify parameters of the waveform 370 such as frequency, amplitude, running time, waveform selection, prescription expiration time, and duty cycle respectively.

The tabs may be tapped/clicked by a user for selecting a particular predetermined waveform as shown in FIGS. 3B and 3C or for selecting a predetermined waveform protocol as shown in FIGS. 3D and 3E. The waveforms and waveform protocols may be loaded by the SCS IPG 106 processor 200 from the waveform library 121 shown in FIG. 1A. The individual waveforms might be, e.g., burst or contour waveforms selected by tapping different tabs. FIG. 3B shows the exemplary predetermined waveform 130e selected by the leftmost tab 350. FIG. 3C shows the predetermined waveform 130f selected by the tab fourth from the Left. FIG. 3D shows a waveform protocol consisting of the predetermined waveforms 130e and 130f selected by the leftmost tab and the tab fourth from the Left. FIG. 3E shows the waveform protocol of FIG. 3D stored as a predetermined protocol and selected by the tab second from the left. In FIG. 3E the tabs select predetermined waveform protocols each consisting of multiple waveforms. FIG. 3F is a waveform protocol editor display for customizing and creating waveform protocols. In FIG. 3F, the user can edit predetermined protocols and create/customize new protocols (e.g., run a first waveform for a first time, run a second waveform for a second time).

Figure 4:
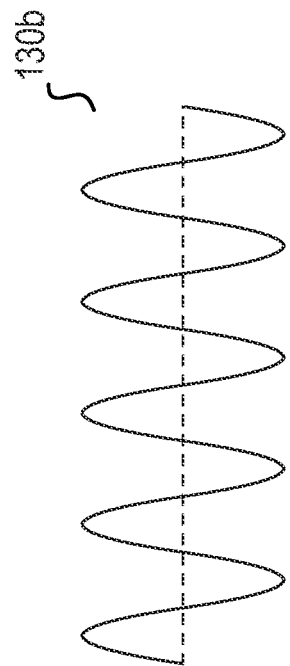
FIGS. 4-7 depict exemplary predetermined waveforms.
Figure 5:
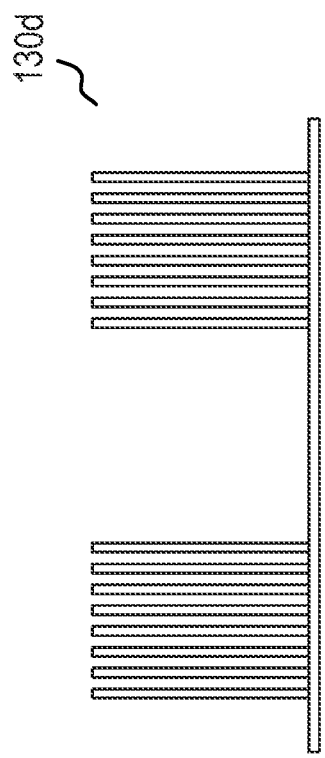
Figure 6:
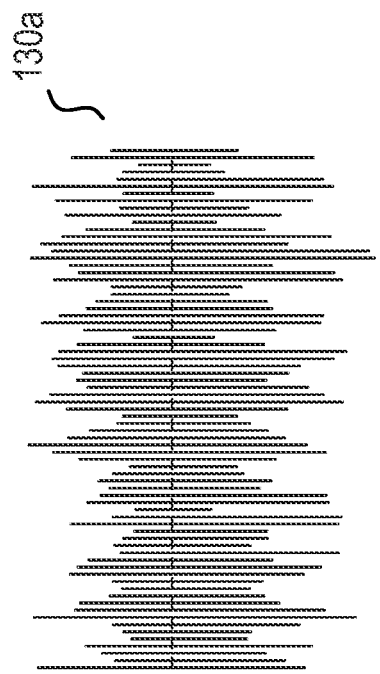
Figure 7:
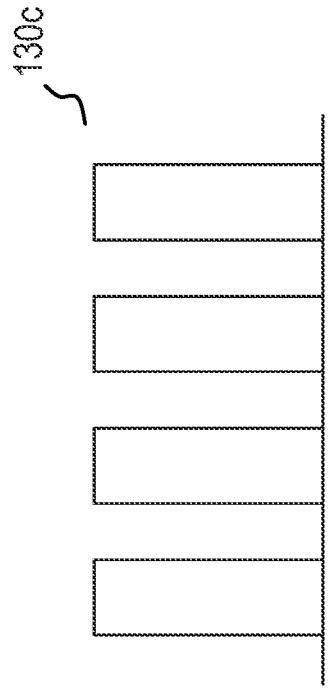

FIGS. 4-7 depict exemplary predetermined waveforms. FIG. 4 shows the exemplary waveform 130a shown in FIG. 1. In FIG. 5 shows the exemplary waveform 130b shown in FIG. 1. In FIG. 6 shows the exemplary waveform 130c shown in FIG. 1. In FIG. 7 shows the exemplary waveform 130d shown in FIG. 1. The exemplary waveforms 130a,b,c,d are retrievably stored in the waveform library 121 shown in FIG. 1. The depicted waveforms 130a,b,c,d are illustrative examples. The waveforms 130a,b,c,d may be any waveform retrievably stored in the waveform library 121 shown in FIG. 1. In illustrative examples, the SCS IPG 106 may be configured to apply any waveform or waveform protocol including waveform types known in the art such as but not limited to, burst, contour, spike, High Frequency and Ultra High Frequency.

Figure 8:
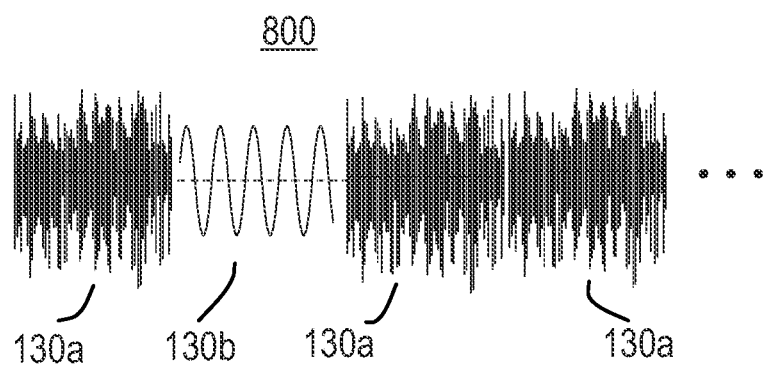
FIGS. 8-9 depict exemplary waveform protocols.
Figure 9:
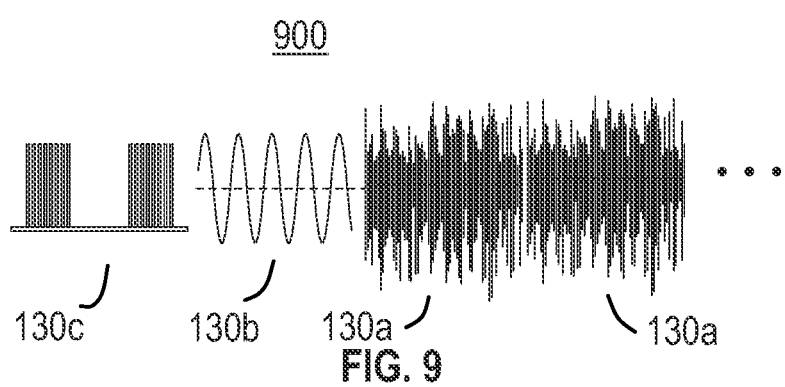

FIGS. 8-9 depict exemplary waveform protocols. In FIG. 8, the exemplary waveform protocol 800 includes the exemplary waveforms 130a and 130b. In the depicted example, the waveform protocol 800 comprises a cycling pattern of alternating waveforms including the waveforms 130a, 130b, 130a and 130a applied by the SCS IPG 106 in the depicted sequence. The waveform sequence of the waveform protocol 800 depicted in FIG. 8 repeats. The waveform sequence of the waveform protocol 800 may be configured to repeat using the SCS IPG 106 until a predetermined expiration time. The waveform protocol 800 may comprise any waveform configured by the SCS IPG 106. In the depicted example the individual waveforms of the exemplary waveform protocol 800 are applied by the SCS IPG 106 in series using the same set of electrodes.

In FIG. 9, the exemplary waveform protocol 900 includes the exemplary waveforms 130a, 130b and 130c. In the depicted example, the waveform protocol 900 comprises a cycling pattern of alternating waveforms including the waveforms 130c, 130b, 130a and 130a applied by the SCS IPG 106 in the depicted sequence. The waveform sequence of the waveform protocol 900 depicted in FIG. 9 repeats. The waveform sequence of the waveform protocol 900 may be configured to repeat using the SCS IPG 106 until a predetermined expiration time. The waveform protocol 900 may comprise any waveform configured by the SCS IPG 106. In the depicted example the individual waveforms of the exemplary waveform protocol 900 are applied by the SCS IPG 106 in series using the same set of electrodes.

Figure 10:
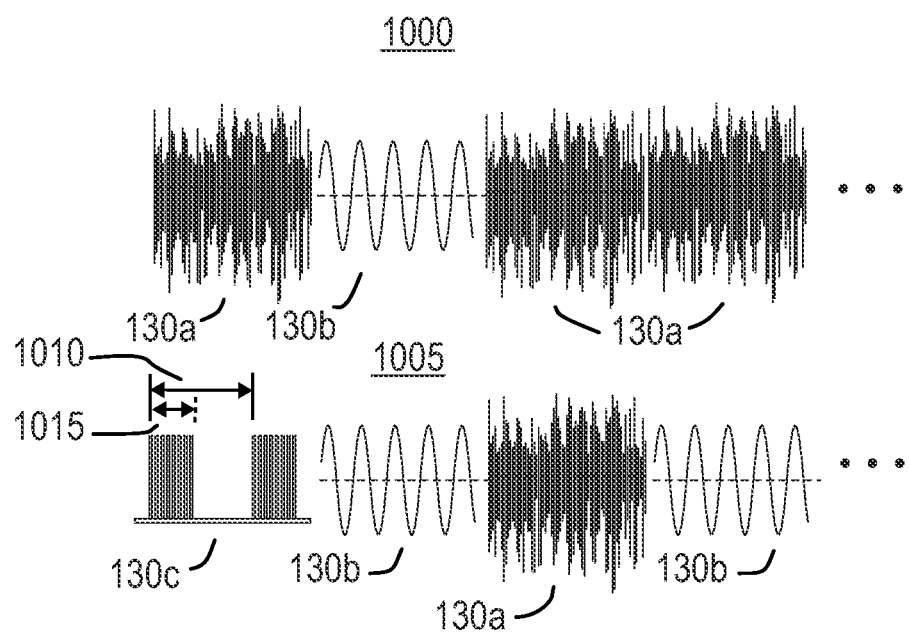
FIG. 10 depicts an example of running two exemplary waveform protocols in parallel using multiple electrode sets.

FIG. 10 depicts an example of running two exemplary waveform protocols in parallel using multiple electrode sets. In FIG. 10, the exemplary waveform protocol 1000 is applied by the SCS IPG 106 using one set of electrodes in electrical connection with one portion of the spinal cord of the patient. The exemplary waveform protocol 1005 is applied by the SCS IPG 106 using a different set of electrodes in electrical connection with a different portion of the spinal cord of the patient. The waveform protocols 1000 and 1005 are applied to the patient spinal cord at the same time in parallel using different sets of electrodes.

Figure 11:
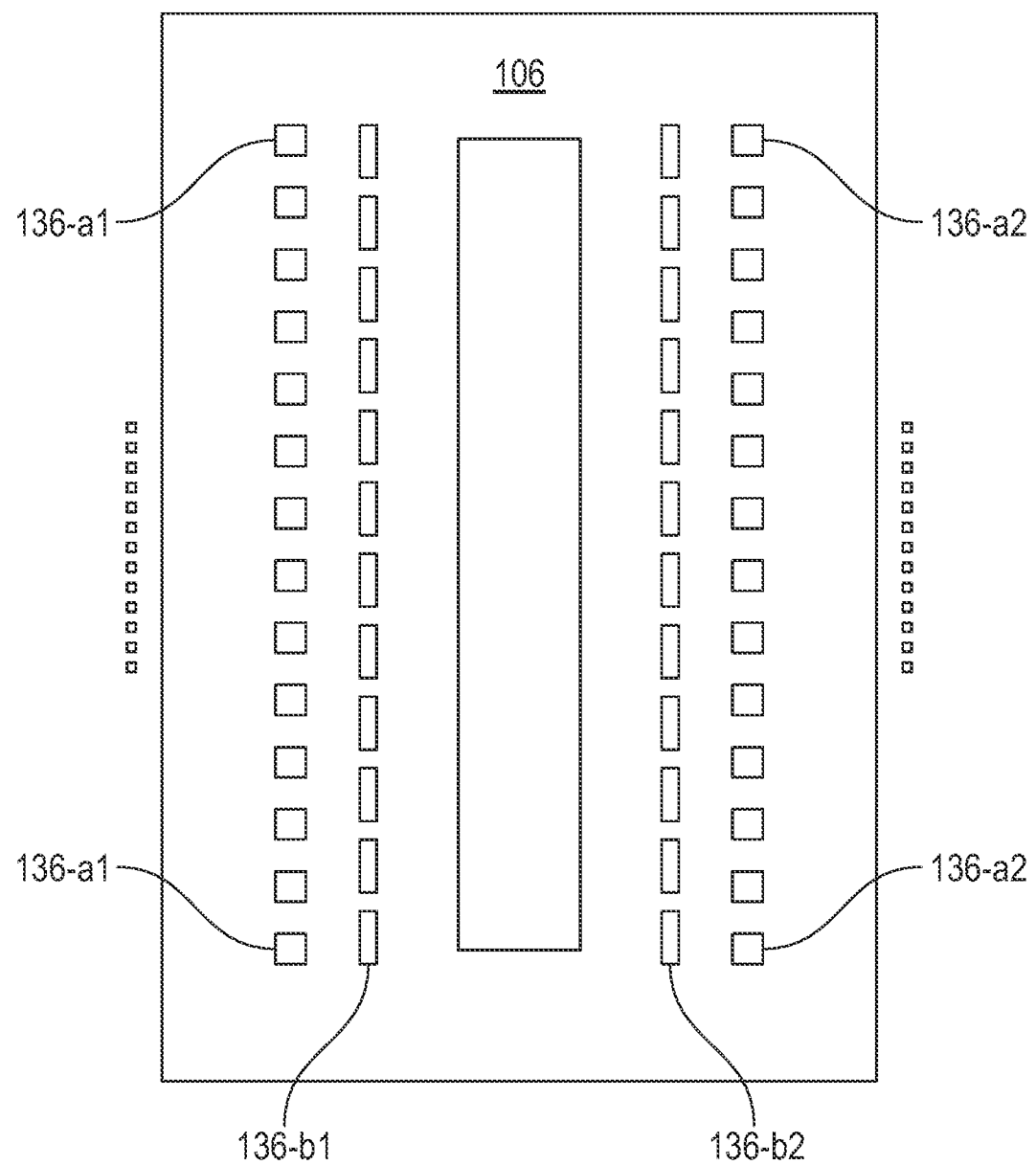
FIG. 11 depicts an exemplary IPG electrode input/output (I/O) interface configured to operate multiple electrode sets.

FIG. 11 depicts an exemplary IPG electrode input/output (I/O) interface configured to operate multiple electrode sets. The IPG electrode I/O interface depicted in FIG. 11 may be implemented in the electrode I/O interface 221 depicted in, at least, FIG. 2. FIG. 11 shows exemplary waveform energy output connections configured in groups 136-a1 and 136-a2, and exemplary waveform energy input connections configured in groups 136-b1 and 136-b2. The waveform energy input connections 136-a1 and 136-a2 may be configured by the SCS IPG 106 processor 200 in subgroups of one or more electrodes. The SCS IPG 106 processor 200 may configure one or more energy output connection from groups 136-a1 and 136-a2 to apply any waveform or group of waveforms in series or parallel. The SCS IPG 106 processor 200 may configure one or more energy input connections from groups 136-b1 and 136-b2 to measure applied waveform energy using one or more electrodes.

Figure 12:
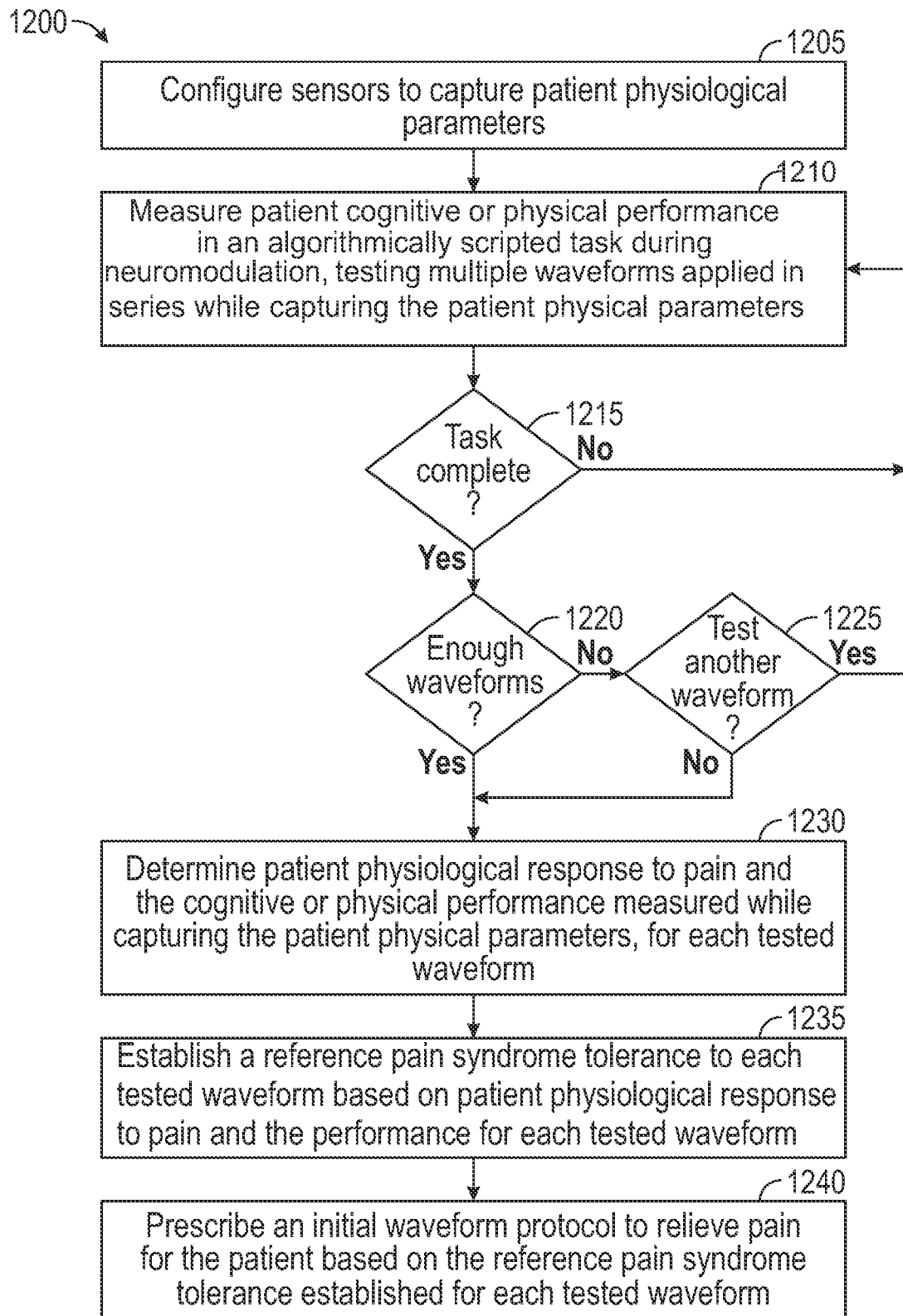
FIG. 12 depicts a process flow of an exemplary waveform protocol prescription engine (WPPE) establishing a reference pain syndrome tolerance to each waveform of a plurality of tested waveforms based on patient physiological or reported response to pain and measured patient task performance for each tested waveform in a trial phase.

FIG. 12 depicts a process flow of an exemplary waveform protocol prescription engine (WPPE) establishing a reference pain syndrome tolerance to each waveform of a plurality of tested waveforms based on patient physiological response to pain and measured patient task performance for each tested waveform in a trial phase.

The method 1200 depicted in FIG. 12 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1200 begins at step 1205 with the processor 200 configuring sensors to capture patient physiological parameters.

Then, the method continues at step 1210 with the processor 200 measuring patient cognitive or physical performance in an algorithmically scripted task during neuromodulation, testing multiple waveforms applied in series while capturing the patient physical parameters.

At step 1215 the processor 200 performs a test to determine if the algorithmically scripted task performed by the patient has been completed. Upon a determination by the processor 200 the algorithmically scripted task performed by the patient has been completed, the method continues at step 1220. Upon a determination by the processor 200 the algorithmically scripted task performed by the patient has not been completed, the method continues at step 1210.

At step 1220 the processor 200 performs a test to determine if enough waveforms have been tested in the trial phase. For example, the processor may compare the number of waveforms tested to a threshold number of waveforms to be tested. The threshold number of waveforms to be tested may be configured in a user interface, for example. Upon a determination by the processor 200 at step 1220 enough waveforms have been tested, the method continues at step 1230. Upon a determination by the processor 200 at step 1220 enough waveforms have not been tested, the method continues at step 1225.

At step 1225 the processor 200 performs a test to determine if another waveform is to be tested. Upon a determination by the processor 200 at step 1225 another waveform is to be tested the method continues at step 1210, otherwise the method continues at step 1230.

At step 1230 the processor 200 determines patient physiological response to pain and the cognitive or physical performance measured while capturing the patient physical parameters, for each tested waveform, and the method continues at step 1235.

At step 1235 the processor establishes a reference pain syndrome tolerance to each tested waveform based on patient physiological response to pain and the performance for each tested waveform, and the method continues at step 1240.

At step 1240 the processor 200 prescribes an initial waveform protocol to relieve pain for the patient based on the reference pain syndrome tolerance established for each tested waveform.

In some implementations the method may repeat.

Figure 13:
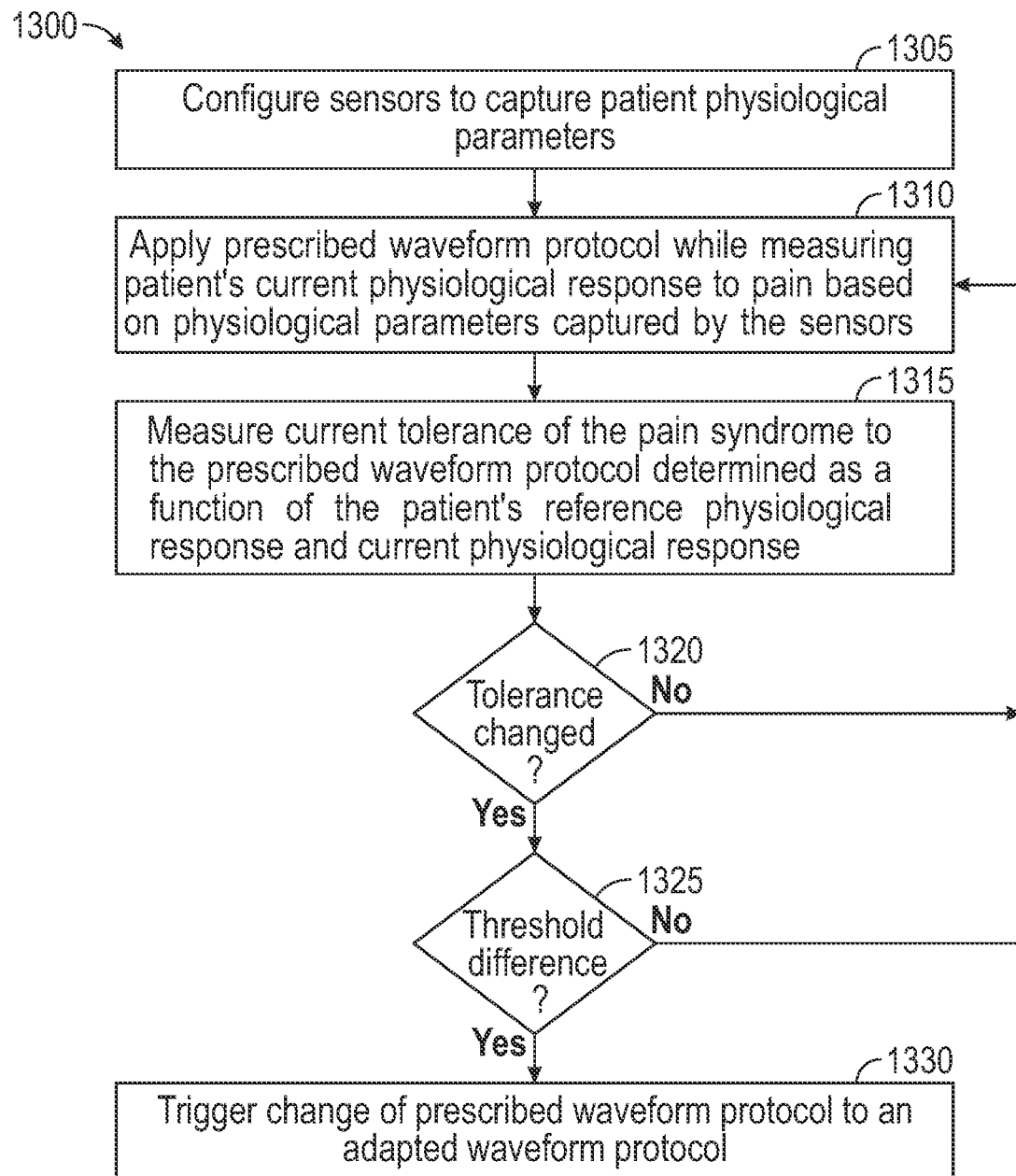
FIG. 13 depicts a process flow of an exemplary waveform protocol prescription engine applying a prescribed predetermined waveform protocol to a patient while measuring the patient's current physiological response to pain, measuring a current tolerance of the pain syndrome to the prescribed predetermined waveform protocol determined as a function of the patient's reference physiological response to pain established in a trial phase and the patient's current physiological response to pain, and in response to determining the tolerance of the pain syndrome to the prescribed predetermined waveform protocol changed by at least a predetermined minimum tolerance threshold difference, triggering a change of the prescribed predetermined waveform protocol to an adapted waveform protocol.

FIG. 13 depicts a process flow of an exemplary waveform protocol prescription engine applying a prescribed predetermined waveform protocol to a patient while measuring the patient's current physiological response to pain, measuring a current tolerance of the pain syndrome to the prescribed predetermined waveform protocol determined as a function of the patient's reference physiological response to pain established in a trial phase and the patient's current physiological response to pain, and in response to determining the tolerance of the pain syndrome to the prescribed predetermined waveform protocol changed by at least a predetermined minimum tolerance threshold difference, triggering a change of the prescribed predetermined waveform protocol to an adapted waveform protocol.

The method 1300 depicted in FIG. 13 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1300 begins at step 1305 with the processor 200 configuring sensors to capture patient physiological parameters.

Then, the method continues at step 1310 with the processor 200 applying a prescribed waveform protocol while measuring patient's current physiological response to pain based on physiological parameters captured by the sensors.

While measuring the patient's current physiological response to pain based on physiological parameters captured by the sensors at step 1315, the processor 200 measures the current tolerance of the pain syndrome to the prescribed waveform protocol determined as a function of the patient's reference physiological response and current physiological response.

At step 1320 the processor 200 performs a test to determine if the tolerance of the pain syndrome to the prescribed waveform protocol changed, based on comparing the patient's current physiological response to pain based on physiological parameters captured by the sensors at step 1315 with the patient's reference physiological response established during a trial phase. Upon a determination by the processor 200 at step 1320 the tolerance of the pain syndrome to the prescribed waveform protocol changed, the method continues at step 1325. Upon a determination by the processor 200 at step 1320 the tolerance of the pain syndrome to the prescribed waveform protocol did not change, the method continues at step 1310.

At step 1325 the processor 200 performs a test to determine if the pain syndrome tolerance change detected by the processor 200 at step 1320 satisfies at least a predetermined threshold difference. Upon a determination by the processor 200 at step 1325 the pain syndrome tolerance change satisfies at least the predetermined threshold difference, the method continues at step 1330, otherwise the method continues at step 1310.

At step 1330, the change in pain syndrome tolerance detected by the processor 200 triggers the processor 200 to change the prescribed waveform protocol to an adapted waveform protocol.

In some embodiments the method may repeat.

Figure 14:
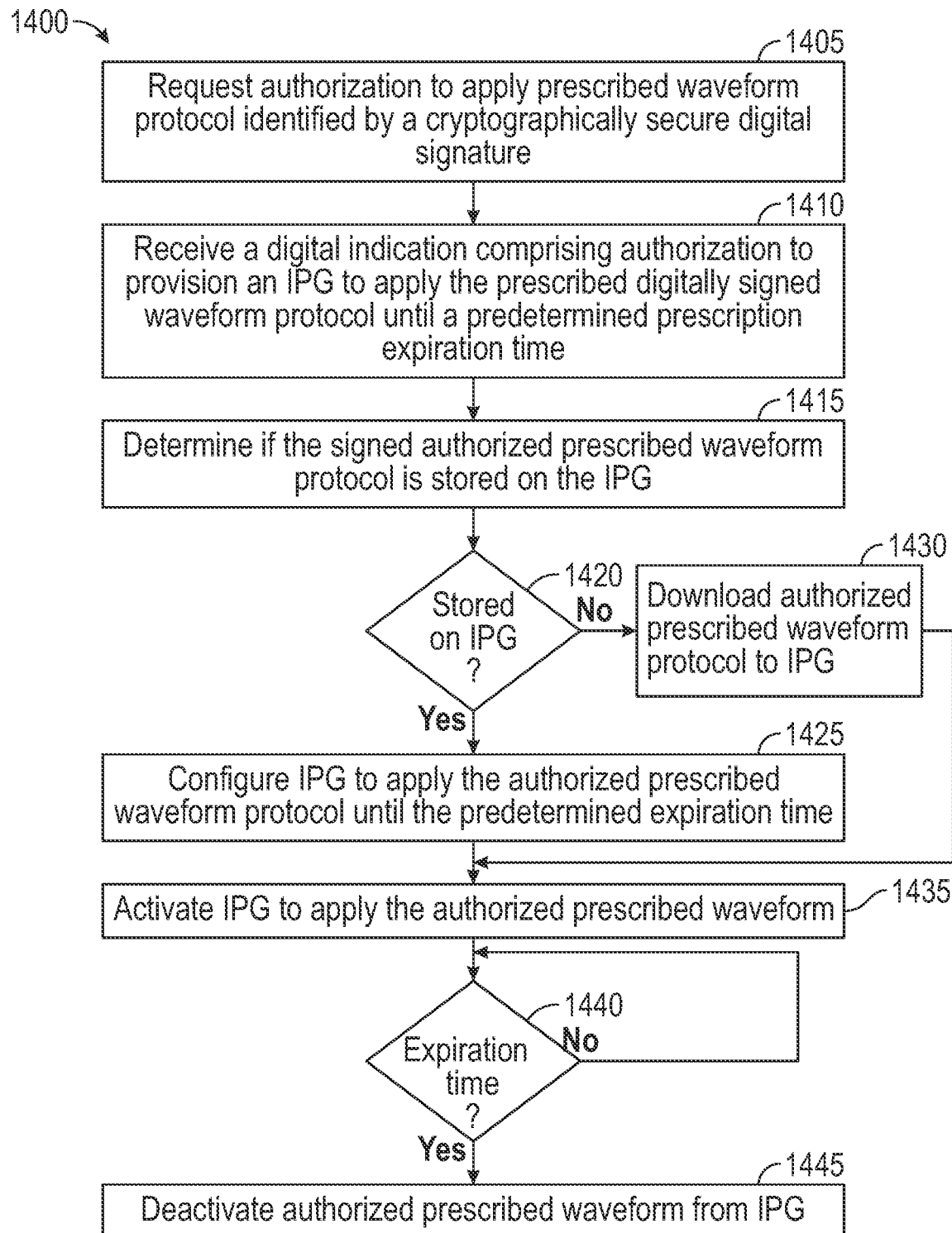
FIG. 14 depicts a process flow of an exemplary waveform protocol prescription engine executing an illustrative scenario obtaining authorization to apply a prescribed predetermined waveform protocol to a patient.

FIG. 14 depicts a process flow of an exemplary waveform protocol prescription engine executing an illustrative scenario obtaining authorization to apply a prescribed predetermined waveform protocol to a patient.

The method 1400 depicted in FIG. 14 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1400 begins at step 1405 with the processor 200 requesting authorization to apply a prescribed waveform protocol identified by a cryptographically secure digital signature. The processor 200 may request the authorization from a server configured to dispense authorizations for prescribing and applying predetermined or licensed waveforms. The processor 200 may request authorization to apply a waveform or waveform protocol selected in a user interface by a doctor. Then, the method continues at step 1410.

At step 1410 the processor 200 receives a digital indication comprising authorization to provision an IPG to apply the prescribed digitally signed waveform protocol until a predetermined prescription expiration time. Then, the method continues at step 1415.

At step 1415 the processor 200 determines if the signed authorized prescribed waveform protocol is stored on the IPG. Then, the method continues at step 1420.

At step 1420 the processor 200 performs a test based on the determination at step 1415, to determine if the signed authorized prescribed waveform protocol should be downloaded to the IPG. Upon a determination by the processor 200 at step 1420 the signed authorized prescribed waveform protocol is stored on the IPG, the method continues at step 1425. Upon a determination by the processor 200 at step 1420 the signed authorized prescribed waveform protocol is not stored on the IPG, the method continues at step 1430.

At step 1430 the processor 200 downloads the signed authorized prescribed waveform protocol to the IPG. Then, the method continues at step 1435.

At step 1425 the processor 200 configures the IPG to apply the authorized prescribed IPG waveform protocol until the predetermined expiration time. Then, the method continues at step 1435.

At step 1435 the processor 200 activates the IPG to apply the authorized prescribed waveform protocol. At step 1435 the processor may configure the IPG with the predetermined expiration time if the waveform was not previously stored on the IPG. Then the method continues at step 1440.

At step 1440 while applying the authorized prescribed waveform protocol the processor 200 performs a test to determine if the predetermined expiration time has been satisfied. Upon a determination by the processor 200 at step 1440 the predetermined expiration time has not been satisfied, the method continues at step 1440. Upon a determination by the processor 200 at step 1440 the predetermined expiration time has been satisfied, the method continues at step 1445.

At step 1445, the processor 200 deactivates the authorized prescribed waveform protocol from the IPG to stop applying the waveform protocol to the patient.

In some embodiments the method may repeat.

Figure 15:
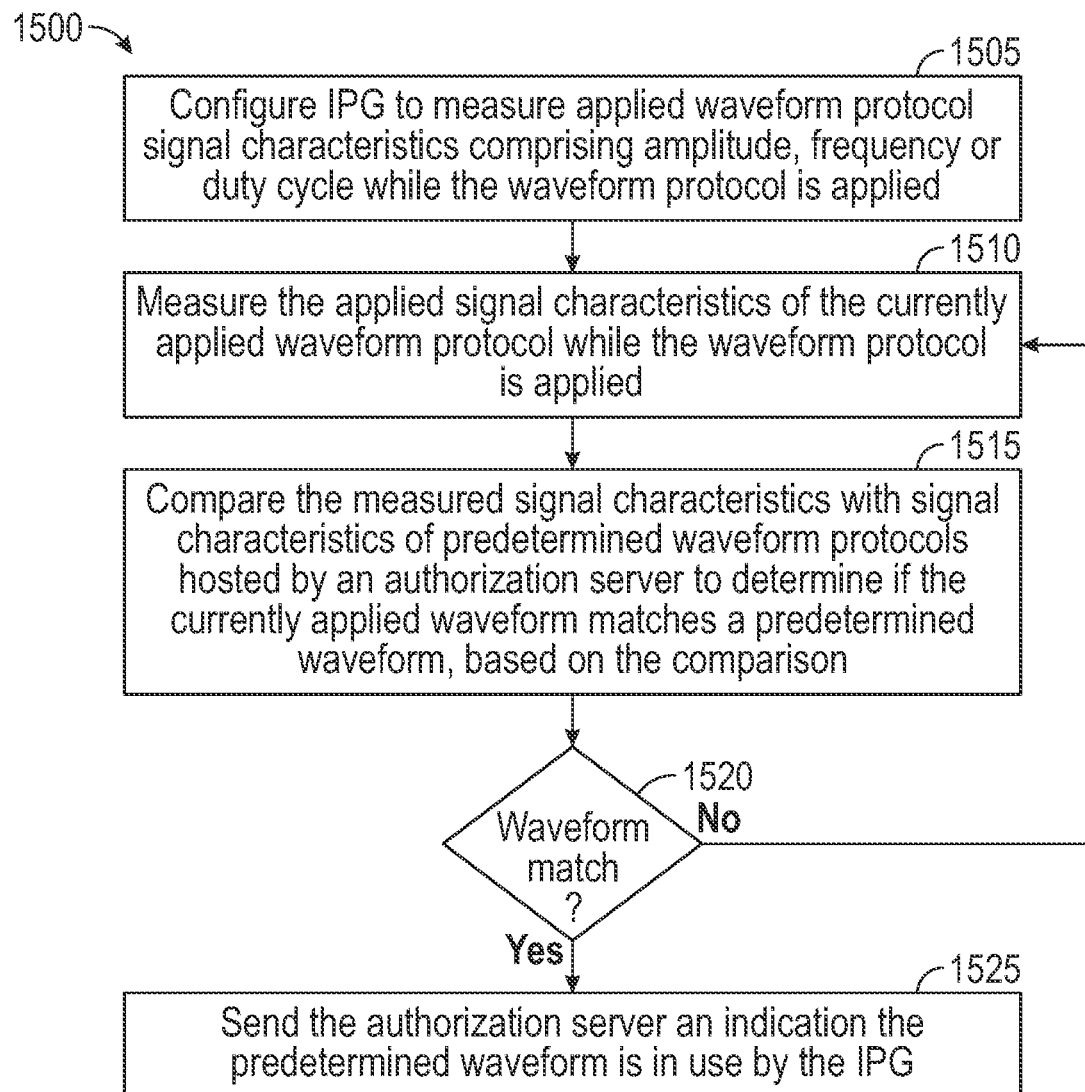
FIG. 15 depicts a process flow of an exemplary waveform protocol prescription engine executing an illustrative scenario detecting use of a predetermined waveform protocol based on measured signal characteristics.

FIG. 15 depicts a process flow of an exemplary waveform protocol prescription engine executing an illustrative scenario detecting use of a predetermined waveform protocol based on measured signal characteristics.

The method 1500 depicted in FIG. 15 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1500 begins at step 1505 with the processor 200 configuring the IPG to measure applied waveform protocol signal characteristics comprising amplitude, frequency or duty cycle while the waveform protocol is applied. Then, the method continues at step 1510.

At step 1510 the processor 200 measures the applied signal characteristics of the currently applied waveform protocol while the waveform protocol is applied. Then, the method continues at step 1515.

At step 1515 the processor 200 compares the measured signal characteristics with signal characteristics of predetermined waveform protocols hosted by an authorization server to determine if the currently applied waveform matches a predetermined waveform, based on the comparison. Then, the method continues at step 1520.

At step 1520 the processor 200 performs a test to determine if the processor 200 should send an indication a predetermined waveform or waveform protocol is in use by the IPG, based on the comparison performed by the processor 200 at step 1515.

At step 1525, upon a determination by the processor 200 at step 1520 the processor 200 should send an indication a predetermined waveform is in use by the IPG, the processor 200 sends the authorization server an indication the predetermined waveform is in use by the IPG. An SCS IPG implementation configured to detect a predetermined waveform or waveform protocol in use may be able to prevent the non-permissive/unauthorized usage of proprietary waveforms.

In some embodiments the method may repeat.

Although various embodiments have been described with reference to the Drawings, other embodiments are possible.

An exemplary method may comprise applying a predetermined waveform protocol (133) to a patient (115) to treat a pain syndrome, while measuring at least one current patient physiological parameter (146) determined as a function of sensor data (145) captured in a feedback loop (143), using a Spinal Cord Stimulation (SCS) Implantable Pulse Generator (IPG) (106) processor (200); determining if a physiologic tolerance of the pain syndrome to the predetermined waveform protocol (133) changed as a function of the at least one current patient physiological parameter (146) measured in the feedback loop (142) and at least one historical patient physiological parameter, using the SCS IPG (106) processor (200); and in response to determining the physiologic tolerance of the pain syndrome to the predetermined waveform protocol (133) changed, triggering a modification of the predetermined waveform protocol (133) to an adapted waveform protocol (157), using the SCS IPG (106) processor (200).

The method may further comprise determining during the feedback loop (143) if the physiologic tolerance of the pain syndrome to the predetermined waveform protocol (133) changed, using the SCS IPG (106) processor (200).

The method may further comprise determining if the physiologic tolerance of the pain syndrome to the predetermined waveform protocol (133) changed based on comparing the at least one current patient physiological parameter (146) measured in the feedback loop (143) with the at least one historical patient physiological parameter, using the SCS IPG (106) processor (200).

The at least one historical patient physiological parameter may be a physiological parameter measured during a previous iteration of the feedback loop (143), using the SCS IPG (106) processor (200).

The at least one historical patient physiological parameter may be a physiological parameter (146) measured during a pre-implant trial phase (148), using the SCS IPG (106) processor (200).

The method may further comprise applying the adapted waveform protocol (157) to the patient (115), using the SCS IPG (106) processor (200).

The at least one current patient physiological parameter (146) may further comprise at least one of: heart rate (HR), heart rate variability (HRV), RR interval (RR), blood pressure (BP), body temperature (TEMP) or oxygen tension (PaO$_2$).

The at least one historical patient physiological parameter (146) may further comprise at least one of: heart rate (HR), heart rate variability (HRV), RR interval (RR), blood pressure (BP), body temperature (TEMP) or oxygen tension (PaO$_2$).

The predetermined waveform protocol (133) may further comprise at least one waveform.

The predetermined waveform protocol (133) may be at least one waveform.

The predetermined waveform protocol (133) may be a plurality of waveforms.

The predetermined waveform protocol (133) may be a plurality of distinct waveforms.

Applying the predetermined waveform protocol (133) may further comprise applying the at least one waveform in a pattern, using the SCS IPG (106) processor (200).

The pattern may further comprise an on-off pattern.

The on-off pattern may further comprise applying the at least one waveform during at least a first time period and not applying the at least one waveform during at least a second time period.

The predetermined waveform protocol (133) may further comprise a plurality of distinct waveforms.

Each waveform of the plurality of distinct waveforms may have at least one signal characteristic.

The at least one signal characteristic may further comprise amplitude, frequency or duty cycle.

Applying the predetermined waveform protocol (133) may further comprise applying the plurality of distinct waveforms in a pattern, using the SCS IPG (106) processor (200).

The pattern may further comprise a cycling pattern.

The cycling pattern may further comprise individually applying each waveform of the plurality of distinct waveforms during a respective time period of a plurality of time periods.

The pattern may further comprise an alternating pattern.

The alternating pattern may further comprise applying a first set of at least one waveform sequentially during a first time period, applying a second set of at least one waveform sequentially during a second time period, wherein the second set of at least one waveform comprises at least one waveform distinct from the first set of at least one waveform.

Applying the plurality of distinct waveforms may further comprise configuring a pulse generator (224) to apply at least one waveform of the plurality of distinct waveforms, using the SCS IPG (106) processor (200).

The method may further comprise configuring a pulse generator (224) to apply a plurality of waveforms using a plurality of electrodes (136), using the SCS IPG (106) processor (200).

The method may further comprise configuring a pulse generator (224) to apply a plurality of waveforms in series, using the SCS IPG (106) processor (200).

Apply the plurality of waveforms in series may further comprise: apply a first waveform using at least one electrode (136) during a first time period; and apply another waveform distinct from the first waveform using the at least one electrode (136) during at least a second time period after the first time period.

The method may further comprise configuring a pulse generator (224) to apply a plurality of waveforms in parallel, using the SCS IPG (106) processor (200).

Apply the plurality of waveforms in parallel may further comprise: apply at least a first waveform during a time period using at least a first electrode (136) set comprising at least one electrode (136) and apply at least another waveform during the time period using at least another electrode (136) set comprising at least one electrode (136) not in the at least the first electrode (136) set, wherein the at least another waveform is distinct from the at least the first waveform.

The method may further comprise receiving a digital indication comprising a selection of at least one predetermined waveform protocol (133), using the SCS IPG (106) processor (200).

The selected at least one predetermined waveform protocol (133) may further comprise a plurality of distinct waveforms.

The received digital indication may further comprise a run time for at least one waveform of the plurality of distinct waveforms.

The method may further comprise applying the at least one waveform for the run time before applying at least another waveform, using the SCS IPG (106) processor (200).

The method may further comprise configuring a pulse generator (224) to apply the selected at least one predetermined waveform protocol (133), using the SCS IPG (106) processor (200).

The received digital indication may further comprise an indication to apply the plurality of distinct waveforms using a respective plurality of electrode (136) sets configured to apply the plurality of distinct waveforms in parallel.

The digital indication may further comprise an indication to apply the plurality of distinct waveforms in series.

The method may further comprise receiving the selection of the at least one predetermined waveform protocol (133) from a user interface.

The digital indication may further comprise an indication to apply the plurality of distinct waveforms in a pattern.

The pattern may further comprise an alternating pattern.

The alternating pattern may further comprise applying the plurality of distinct waveforms one waveform at a time in sequence.

The received digital indication may further comprise an indication of an ordinal position of each waveform of the plurality of distinct waveforms in the sequence.

The pattern may further comprise a cycling pattern.

The cycling pattern may further comprise individually applying each waveform of the plurality of distinct waveforms during a single time period of a respective plurality of time periods.

The user interface may be configured in a computing device remote from the SCS IPG (106).

The received digital indication may further comprise at least one parameter of at least one waveform of the plurality of distinct waveforms.

The at least one parameter may further comprise one or more of amplitude, frequency, or duty cycle.

The at least one parameter of the at least one predetermined waveform protocol (133) may further comprise a limitation on one or more of electric current, voltage, or power.

The method may further comprise capturing sensor data measuring patient physiological response to pain, using the SCS IPG (106) processor (200).

The method may further comprise capturing the sensor data during a neuromodulation trial procedure (148).

The sensor data may be pre-implant sensor data.

The method may further comprise: configuring at least one sensor to capture at least one patient (115) physiological parameter (146), using the SCS IPG (106) processor (200); measuring patient (115) cognitive or physical performance in a task during a neuromodulation session in a trial phase (148), using the SCS IPG (106) processor (200); testing multiple waveforms to be applied in series in the trial phase (148) while capturing the at least one patient (115) physiological parameter (146), using the SCS IPG (106) processor (200); determining patient (115) physiological response to pain and the cognitive or physical performance measured while capturing the at least one patient (115) physiological parameter (146) in the trial phase (148), for each tested waveform, using the SCS IPG (106) processor (200); establishing a reference pain syndrome tolerance to each tested waveform based on patient (115) physiological response to pain and the measured performance for each tested waveform in the trial phase (148), using the SCS IPG (106) processor (200); and prescribing an initial predetermined waveform protocol (133) to relieve pain for the patient (115) based on the reference pain syndrome tolerance established in the trial phase (148) for each tested waveform, using the SCS IPG (106) processor (200).

The trial phase (148) may further comprise establishing the reference pain syndrome tolerance to each tested waveform for a plurality of different output electrode configurations for each tested waveform, using the SCS IPG (106) processor (200).

The task may further comprise an algorithmically scripted interactive task comprising a game or test presented to the patient (115) via a mobile device (166) operably coupled with the SCS IPG (106).

Establishing the reference pain syndrome tolerance may further comprise: sampling the captured at least one patient (115) physiological parameter (146) while the patient (115) performs the task and storing the samples as a physiological parameter (146) time series, using the SCS IPG (106) processor (200); and storing the measured cognitive or physical performance with the physiological parameter (146) time series, using the SCS IPG (106) processor (200).

The neuromodulation session may further comprise: applying each tested waveform for an active application time period and not applying each tested waveform for an inactive application time period; wherein the method further comprises: storing the physiological parameter (146) time series sampled during the active application time period as an active application physiological parameter (146) time series with the cognitive or physical performance measured during the active application time period; storing the physiological parameter (146) time series sampled during the inactive application time period as an inactive application physiological parameter (146) time series with the cognitive or physical performance measured during the inactive application time period; and establishing the reference pain syndrome tolerance to the tested waveform as a reference pain syndrome tolerance time series determined as a function of the active application physiological parameter (146) time series and the inactive application physiological parameter (146) time series.

Establishing the reference pain syndrome tolerance may further comprise: sending an indication to a mobile device (166) to request measured cognitive or physical performance data in response to determining a waveform under test has been applied for a predetermined individual waveform test time period, using the SCS IPG (106) processor (200); and receiving the requested measured cognitive or physical performance data related to the waveform under test from the mobile device (166), using the SCS IPG (106) processor (200).

Prescribing may further comprise prescribing, using the SCS IPG (106) processor (200), the initial predetermined waveform protocol (133) predicted by a machine learning model to optimize a pain syndrome treatment goal selected from the group consisting of maximum relief from pain and highest resistance to pain syndrome tolerance, wherein the machine learning model is configured to determine the prediction as a function of the active application physiological parameter (146) time series and the inactive application physiological parameter (146) time series.

The method may further comprise: configuring at least one sensor to capture at least one patient (115) physiological parameter (146), using the SCS IPG (106) processor (200); applying a prescribed predetermined waveform protocol (133) while measuring the patient (115) current physiological response to pain based on at least one physiological parameter (146) captured by the at least one sensor, using the SCS IPG (106) processor (200); measure a current tolerance of the pain syndrome to the prescribed predetermined waveform protocol (133) determined as a function of a patient (115) reference physiological response to pain established in the trial phase (148) and the patient (115) current physiological response to pain, using the SCS IPG (106) processor (200); and in response to determining the tolerance of the pain syndrome to the prescribed predetermined waveform protocol (133) changed by at least a predetermined minimum tolerance threshold difference, trigger change of the prescribed predetermined waveform protocol (133) to an adapted waveform protocol (157), using the SCS IPG (106) processor (200).

Measure the current tolerance of the pain syndrome to the prescribed predetermined waveform protocol (133) may further comprise: sampling the captured at least one patient (115) physiological parameter (146) and storing the samples as a treatment phase physiological parameter (146) time series, using the SCS IPG (106) processor (200).

The method may further comprise determining the current tolerance of the pain syndrome to the prescribed predetermined waveform protocol (133) as a function of the treatment phase physiological parameter (146) time series and an active application physiological parameter (146) time series captured in the trial phase (148).

Measure the current tolerance of the pain syndrome to the prescribed predetermined waveform protocol (133) may further comprise determine a sample-by-sample difference time series based on comparing at least a portion of the treatment phase physiological parameter (146) time series and the active application physiological parameter (146) time series captured in the trial phase (148) for the prescribed predetermined waveform protocol (133).

The method may further comprise determining at least one statistical measure of the sample-by-sample difference time series.

The method may further comprise determining if the tolerance of the pain syndrome to the prescribed predetermined waveform protocol (133) changed by at least the predetermined minimum tolerance threshold difference, based on the at least one statistical measure.

The change of the prescribed predetermined waveform protocol (133) to the adapted waveform protocol (157) may further comprise modifying at least one signal characteristic of at least one waveform of the prescribed predetermined waveform protocol (133).

The modified at least one signal characteristic of the at least one waveform of the prescribed predetermined waveform protocol (133) may further comprise one or more of: amplitude, power, frequency, waveshape, duty cycle, start time in a sequence or end time in a sequence.

The change of the prescribed predetermined waveform protocol (133) to the adapted waveform protocol (157) may further comprise reassigning at least one waveform or waveform protocol to a different set of electrodes.

The trial phase (148) may further comprise establishing the reference pain syndrome tolerance to each tested waveform for a plurality of different output electrode configurations for each tested waveform, using the SCS IPG (106) processor (200).

The method may further comprise: requesting authorization to apply a prescribed predetermined waveform protocol (133) identified by a cryptographically secure digital signature, using the SCS IPG (106) processor (200); receiving a digital indication comprising authorization to provision the SCS IPG (106) to apply the authorized digitally signed prescribed predetermined waveform protocol (133) until a predetermined prescription expiration time, using the SCS IPG (106) processor (200); and configuring the SCS IPG (106) to apply the authorized digitally signed prescribed predetermined waveform protocol (133) until the predetermined prescription expiration time, using the SCS IPG (106) processor (200).

The method may further comprise receiving a digital indication comprising a selection of a prescribed predetermined waveform protocol (133) to be applied by the SCS IPG (106).

The method may further comprise receiving the digital indication comprising the selection of the prescribed predetermined waveform protocol (133) via a communication network.

The method may further comprise receiving the digital indication comprising the selection of the prescribed predetermined waveform protocol (133) from a user interface.

The method may further comprise receiving the digital indication comprising the selection of the prescribed predetermined waveform protocol (133) from a mobile app.

The digital indication comprising the selection of the prescribed predetermined waveform protocol (133) may further comprise a configuration mapping of individual waveforms of the prescribed predetermined waveform protocol (133) to individual electrodes.

The digital indication comprising the selection of the prescribed predetermined waveform protocol (133) may further comprise a plurality of configuration mappings of individual waveforms of the prescribed predetermined waveform protocol (133) to individual electrodes.

The method may further comprise activating the SCS IPG (106) to apply the authorized digitally signed prescribed predetermined waveform protocol (133), using the SCS IPG (106) processor (200).

The method may further comprise activating the SCS IPG (106) to apply the authorized digitally signed prescribed predetermined waveform protocol (133), using the SCS IPG (106) processor (200) to energize at least one individual electrode with a particular waveform of the authorized digitally signed prescribed predetermined waveform protocol (133), wherein the particular waveform was assigned to the at least one individual electrode by a digital prescription received by the SCS IPG (106).

The method may further comprise activating the SCS IPG (106) to apply the authorized digitally signed prescribed predetermined waveform protocol (133), using the SCS IPG (106) processor (200) to energize each electrode of a plurality of electrodes with a different particular waveform of the authorized digitally signed prescribed predetermined waveform protocol (133), wherein each different particular waveform was assigned to each electrode of the plurality of electrodes by a digital prescription received by the SCS IPG (106).

The method may further comprise: determining if the predetermined prescription expiration time is satisfied, using the SCS IPG (106) processor (200); and in response to determining the predetermined prescription expiration time is satisfied, deactivate the authorized digitally signed prescribed predetermined waveform protocol (133) from the SCS IPG (106), using the SCS IPG (106) processor (200).

The method may further comprise configuring the SCS IPG (106) to apply a default predetermined waveform protocol (133) after the predetermined prescription expiration time, using the SCS IPG (106) processor (200).

The default predetermined waveform protocol (133) may be a prescribed predetermined waveform protocol (133) distinct from the authorized digitally signed prescribed predetermined waveform protocol (133).

The method may further comprise: determining if the authorized digitally signed prescribed predetermined waveform protocol (133) is stored on the SCS IPG (106); in response to determining the authorized digitally signed prescribed predetermined waveform protocol (133) is stored on the SCS IPG (106), activating the SCS IPG (106) to apply the authorized digitally signed prescribed predetermined waveform protocol (133), using the SCS IPG (106) processor (200); and in response to determining the authorized digitally signed prescribed predetermined waveform protocol (133) is not stored on the SCS IPG (106), downloading the authorized digitally signed prescribed predetermined waveform protocol (133) to the SCS IPG (106), using the SCS IPG (106) processor (200).

The method may further comprise: configuring the SCS IPG (106) to measure at least one signal characteristic of at least one waveform, using the SCS IPG (106) processor (200); measuring the at least one signal characteristic of the at least one waveform while the waveform is applied, using the SCS IPG (106) processor (200); comparing the measured at least one signal characteristic with at least one signal characteristic of at least one predetermined waveform to determine if the currently applied at least one waveform matches the at least one predetermined waveform, based on the comparison; and in response to determining the currently applied at least one waveform matches the at least one predetermined waveform, sending an indication the predetermined waveform is in use by the SCS IPG (106), using the SCS IPG (106) processor (200).

The at least one applied waveform may be a plurality of distinct waveforms comprising a predetermined waveform protocol (133).

Measuring the at least one signal characteristic may further comprise sampling in the time domain, using the SCS IPG (106) processor (200).

Measuring the at least one signal characteristic may further comprise sampling in the frequency domain, using the SCS IPG (106) processor (200).

The at least one signal characteristic of the at least one applied waveform may further comprise at least one of: amplitude, frequency or duty cycle.

The at least one predetermined waveform may be hosted by an authorization server.

Sending the indication the predetermined waveform is in use may further comprise sending the indication to an authorization server, using the SCS IPG (106) processor (200).

Comparing the measured at least one signal characteristic may further comprise determining a correlation of a measured waveform power spectrum with a predetermined waveform power spectrum, using the SCS IPG (106) processor (200).

Comparing may further comprise a frequency-bin by frequency bin comparison of amplitudes in the measured waveform power spectrum with the predetermined waveform power spectrum, using the SCS IPG (106) processor (200).

The method may further comprise determining the correlation in the frequency domain, using the SCS IPG (106) processor (200).

The method may further comprise determining a correlation coefficient value of at least 0.75 indicates the currently applied at least one waveform matches the at least one predetermined waveform, using the SCS IPG (106) processor (200).

The method may further comprise configuring a minimum correlation coefficient threshold value that must be reached to determine the currently applied at least one waveform matches the at least one predetermined waveform.

The method may further comprise determining the correlation in a predetermined passband width, using the SCS IPG (106) processor (200).

The predetermined passband width may be a configurable passband width, using the SCS IPG (106) processor (200).

The method may further comprise configuring the passband width to a passband width received with a digital indication from a user interface, using the SCS IPG (106) processor (200).

The method may further comprise: receiving sensor information (145) comprising the physiological response of the patient (115) to pain from at least one sensor, using the SCS IPG (106) processor (200); comparing the received sensor information (145) from the at least one sensor to reference sensor information (145) comprising the physiological response of the patient (115) captured when the patient (115) was not experiencing a pain crisis, to determine if the patient is experiencing a pain crisis based on the comparison, using the SCS IPG (106) processor (200); in response to determining the patient (115) is experiencing a pain crisis, activating at least one effector (139) configured to change spinal cord (112) activity based on providing external stimulation to the patient (115), using the SCS IPG (106) processor (200); and adjusting the external stimulation to the patient (115) to mitigate the pain crisis, using the SCS IPG (106) processor (200).

The at least one sensor may be configured to measure at least one of: blood pressure, heart rate or oxygen tension.

The at least one sensor may further comprise at least one wearable sensor.

The at least one wearable sensor may further comprise a hat configured to capture brain waves (EEG).

The at least one wearable sensor may further comprise a wrist band.

The at least one wearable sensor may further comprise an effector (139) configured to provide external stimulation to the patient (115).

The effector may be a hat configured to provide extracranial stimulation.

The effector may be a wrist band configured to provide acupressure.

The at least one wearable sensor may be in physical contact with the patient (115).

The at least one wearable sensor may further comprise at least one effector (139).

The at least one effector (139) may be a vagal nerve stimulator, an acupressure stimulator or an extracranial stimulator.

Adjusting the external stimulation to the patient (115) may further comprise adjusting intensity of the external stimulation to the patient (115), using the SCS IPG (106) processor (200).

Adjusting the external stimulation to the patient (115) may further comprise adjusting frequency of the external stimulation to the patient (115), using the SCS IPG (106) processor (200).

Adjusting the external stimulation to the patient (115) may further comprise modulating the external stimulation to the patient (115) in an on/off pattern, using the SCS IPG (106) processor (200).

Adjusting the external stimulation to the patient (115) may further comprise activating more than one effector (139) to provide the external stimulation to the patient (115), using the SCS IPG (106) processor (200).

The method may further comprise communicatively pairing the at least one sensor with the SCS IPG (106) processor (200).

The method may further comprise communicatively pairing the at least one effector with the SCS IPG (106) processor (200).

The method may further comprise communicatively pairing the at least one sensor with a mobile device (166) operably coupled with the SCS IPG (106).

The method may further comprise communicatively pairing the at least one effector with a mobile device (166) operably coupled with the SCS IPG (106).

The method may further comprise: in response to determining the patient (115) is experiencing the pain crisis, triggering an application configured in a mobile device (166) of the patient to display heart rate or blood pressure to the patient while interacting with the patient (115) in an algorithmically scripted biofeedback scenario designed to help the patient (115) calm themselves by reducing their heart rate or blood pressure.

The method may further comprise triggering an application configured in the mobile device (166) of the patient to play music or other content that has been determined to calm the patient.

Spinal Cord Stimulation (SCS) devices may be used to improve chronic pain syndromes. An SCS device may be a peripheral stimulation device. Some SCS devices may comprise an Implantable Pulse Generator (IPG). An SCS IPG may be configured with leads designed to stimulate a patient's spinal cord with electrical energy. The electrical energy may be delivered to the spinal cord in the form of an electrical waveform generated by the SCS IPG.

An SCS IPG may be implanted in a patient. Some patients may develop tolerance for a particular waveform. A waveform that a patient has developed tolerance for may not be effective to reduce pain for that patient. A patient that has developed tolerance for a particular waveform may need to have an implanted SCS IPG explanted, or surgically removed, and replaced with another SCS IPG that can use another more effective waveform.

Disclosed herein is an Open Label SCS IPG device which is capable of downloading and/or uploading and running multiple existing waveforms and using the waveforms to improve chronic pain syndromes. An exemplary Open Label SCS IPG may be capable of downloading and/or uploading patented waveforms from different companies after the appropriate permission is granted to do so. There may need to be an agreement in place to download patented waveforms on this device, after which the waveforms can be run in individualized frequencies to maximize patient benefit.

The invention relates to receiving a digital indication comprising authorization to use at least two predetermined waveforms as input to an Open Label implantable pulse generator (IPG) configured for multiple waveform spinal cord stimulation (SCS), using a computing device operably coupled with the IPG; downloading and storing the at least two waveforms to the computing device and unlocking the IPG using code executing on the computing device to run the at least two waveforms on the IPG using an individualized alternating or cycling waveform protocol customized using the computing device; and using the individualized protocol with the IPG to limit physiologic tolerance to individual waveforms while stimulating a spinal cord.

Waveform signals may be customized or edited using the computing device. The Open Label SCS IPG may be configured to self-adjust individualized protocols with different waveforms and stimulation patterns based on closed loop techniques using patient feedback, advantageously discovering effective protocols and preventing tolerance.

The user may be enabled to edit or splice the waveforms. Various implementations may permit waveforms to be edited/created and automatic cycling of patented (downloadable) waveforms may be edited. Once waveforms are uploaded into the Open Label SCS IPG they can be modified or remain unchanged. However, the Open Label SCS IPG can run the uploaded waveforms in series or parallel, customized to the needs of the patient. An Open Label SCS IPG implementation may be configured to autonomously adjust waveforms using closed loop waveform adjustment algorithms that may be enabled by a programmer/patient/healthcare personnel. The closed loop algorithms may be turned off by a programmer/patient/healthcare personnel. In some examples the closed loop algorithm implementation may be a software application downloadable to the Open Label SCS IPG to run on the Open Label SCS IPG.

One possible IPG closed loop algorithm implementation may run a test pattern of unmodified waveforms 1, 2, 3, 2, 1, 2, . . . and then obtain evaluation criteria for example asking the patient to indicate how well that treatment worked or determine over time if the patient developed tolerance, and then change future repetition patterns based on whether or how well that test pattern worked. However, closed loop is a different technology that self-adjusts waveform energy depending on patient position (breathing, sitting, standing, walking). The running of waveforms 1,2,3, 2,1,2 should be pre-set by a healthcare worker to determine patient safety, then once it is determined that the patient can benefit from/tolerate that waveform sequence it will be introduced into the IPG memory as a profile that can be turned on/off by the patient or programmer. An exemplary IPG implementation may be configured to run different licensed waveforms, that are currently not able to be run on any currently existing IPG.

In one embodiment, the Open Label SCS IPG is configured to download and run a plurality of waveforms licensed from a respective plurality of IPG manufacturers. The plurality of waveforms is configured to run on the Open Label SCS IPG in an alternating or cycling pattern customized to a patient to prevent the patient from developing tolerance for individual waveforms.

In another embodiment, the Open Label SCS IPG is configured to download pre-existing waveforms and run the pre-existing waveforms in series or parallel to apply the waveforms using an algorithmically determined waveform protocol. The waveform protocol may be algorithmically determined to cycle, alternate, or vary the waveforms to reduce pain syndrome tolerance to the waveform. A feedback function assessing pain, sleep, and Heart Rate (HR) determined using sensor data may be configured to trigger a pre-programmed change in the waveform(s) protocol.

The Open Label SCS IPG may be configured with a BLUETOOTH connection to a tablet computer for waveform analysis and programming.

Any of the foregoing implementations can be employed individually or in conjunction. An SCS IPG implementation in accordance with the present disclosure may achieve one or more technical effects. For example, some implementations may improve accuracy measuring the tolerance of a patient's pain syndrome to a predetermined waveform. Such improved accuracy measuring the pain syndrome tolerance to a predetermined waveform may be a result of measuring patient physiological parameters in a feedback loop using sensors to determine the patient's current physiological response to pain. For example, using sensor data to determine the patient's current physiological response to pain may provide more accurate automatic measurements of a waveform's effectiveness over time. Such automatic measurements of a patient's current physiological response to pain based on sensor data may improve the usefulness of measuring the patient's level of pain. Such improved usefulness of measuring the patient's level of pain may be a result of replacing or supplementing subjective, patient-reported pain levels with captured sensor data representing the patient's current physiological response to pain. For example, measured pain levels based on captured sensor data representing the patient's current physiological response to pain may provide a pain measurement that is more accurate than subjective, patient-reported pain levels provided by a patient over time for a particular pain syndrome. Measuring the patient's current physiological response to pain determined as a function of sensor data captured during a treatment phase and comparing the current physiological response to pain with the patient's reference physiological response to pain determined as a function of sensor data captured during a trial phase may improve the usefulness and responsiveness of neuromodulation therapy. For example, based on comparing the current physiological response over time with the historical physiological response, an SCS IPG implementation in accordance with the present disclosure may detect a change in the tolerance of the patient's pain syndrome more quickly than a patient could self-report. Such an SCS IPG may be able to trigger a change of the predetermined waveform protocol to an adapted waveform protocol more quickly than a patient could self-report increased pain. For example, the SCS IPG may trigger a change of the predetermined waveform protocol to an adapted waveform protocol before the patient would be aware of increased pain. This facilitation may be a result of replacing or supplementing subjective, patient-reported pain levels with captured sensor data representing the patient's physiological response to pain in the feedback loop, permitting the SCS IPG to detect and react to trends in the patient physiological response to pain.

An exemplary Open Label Spinal Cord Stimulator (SCS) Implantable Pulse Generator (IPG) implementation may be configured to run all waveforms in a customizable format. An SCS IPG implementation may be configured to download pre-existing waveforms and run the pre-existing waveforms in series or parallel to apply the waveforms using an algorithmically determined waveform protocol. The waveform protocol may be algorithmically determined to cycle, alternate, or vary the waveforms to reduce pain syndrome tolerance to the waveform. A feedback function assessing pain, sleep, and Heart Rate (HR) determined using sensor data would trigger a pre-programmed change in the waveform(s) protocol.

Reference is made herein to particular features of various implementations. It is to be understood that the disclosure of particular features of various implementations in this specification is to be interpreted as including all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

Suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

The phrases "connected to," "coupled to" and "in communication with" refer to any form of interaction between two or more entities, including mechanical, electrical, magnetic, electromagnetic, fluid, chemical and thermal interaction. Two components may be functionally coupled to each other even though they are not in direct contact with each other. The terms "abutting" or "in mechanical union" refer to items that are in direct physical contact with each other, although the items may not necessarily be attached together.

One of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementation of the present disclosure are contemplated for use with any computing device.

An exemplary Open Label SCS IPG may include hardware comprising an IPG configured to run various licensed waveforms in individualized format. An exemplary SCS IPG may comprise software configured to download licensed waveforms. An agreement or contract may be implemented digitally using the device to obtain the required permission to download and use a licensed waveform. An exemplary Open Label SCS IPG may advantageously limit physiologic tolerance in many patients with chronic pain, as a result of the expansion of available waveforms.

An exemplary Open Label SCS IPG may be configured to receive data comprising information captured by at least one sensor. The at least one sensor may comprise one or more of: a Digital wristband, a Digital vagal sleep sensor, and Digital Hat with EEG sensors. The depicted Open Label SCS IPG comprises software configured to download pre-existing SCS waveforms as well as vagal stimulators and extracranial stimulation. An agreement or contract may be implemented digitally using the device to download and use a licensed waveform. The depicted exemplary Open Label SCS IPG may advantageously limit pain syndrome physiologic tolerance in many patients with a chronic pain syndrome, based on decreasing pain by direct electric communication with the spinal cord through adapting differential waveforms. Various Open Label SCS IPG implementations may be configured to download pre-existing waveforms and run the pre-existing waveforms singularly, in parallel, or in series. The device may be configured to autonomously change waveforms or sequences of waveforms based on measuring specific changes in patient physiology (HR, RR, REM sleep, body position, and temperature). In an illustrative example HR, RR, REM sleep may be captured by a digital wristband, vagal sleep sensor, and hat with EEG sensors and the information will be relayed to the Open Label SCS IPG. An Open Label SCS IPG system may be configured to create bidirectional information transfer. For example, the Open Label SCS IPG may be configured to receive information from the sensors to change spinal cord activity and also deliver information to the EEG and sleep sensors to alter sleep and provide extracranial therapy. The Open Label SCS IPG may autonomously change waveforms or waveform frequency depending on physiologic parameters that suggest increased pain.

An exemplary Open Label SCS IPG may be configured to self-adjust different waveforms based on closed loop technology. The Open Label SCS IPG may be designed to enable downloading of the waveforms over a protected Wi-Fi connection. The Open Label SCS IPG may be configured to permit waveform configurations and programming easy enough for a clinician to perform, instead of the practice based on current technology requiring skilled representatives from neuromodulation companies to perform complex programming). Various implementations may be configured to run waveforms in a protocol designed to use less energy, by running waveforms less often or only when needed as determined based on sensor data, thereby permitting an increase in the Open Label SCS IPG battery life. Some designs may comprise software configured to permit a clinician to create and evaluate new waveforms and export the new waveforms to a database or another IPG, to expand any current IPG's capability to improve chronic pain syndromes.

An exemplary Open Label SCS IPG may be configured to customize a protocol designed to apply multiple waveforms in combination to work in together in a cycling or customizable manner. The multiple waveforms may be applied in series or in parallel. Multiple waveforms may be applied in parallel to energize multiple respective lead sets wherein each lead set delivers energy from one of the waveforms at a time to a portion of a spinal cord. The portion of the spinal cord that the energy from each waveform is delivered to may be different for each lead set.

An Open Label SCS IPG may be configured to use wearable body technology to assess physiologic change. An Open Label SCS IPG may be configured to deliver information to the wearable technology to enact change in physiology. An Open Label SCS IPG may be configured to unlock a device to run multiple pre-existing or predetermined waveforms that reduce cost and increase effectiveness by comparison with current designs.

An Open Label SCS IPG may be configured to use patient physiology from wearable sensors to enact changes in SCS outflow to minimize tolerance. An Open Label SCS IPG may be configured to effect physiologic parameters known to influence chronic pain such as sleep and headache. An Open Label SCS IPG may be configured to allow downloading of the new waveform(s) via BLUETOOTH/internet or other protected connection, permitting a patient to obtain the benefit from the new waveforms without reoperation or explantation of their existing IPG. An Open Label SCS IPG implementation may be configured with an electronic wristband and the bidirectional vagal and cranial stimulators. An Open Label SCS IPG may be configured to self-adjust different waveforms based on closed loop technology from wearable technology sensors. An Open Label SCS IPG may be configured to allow downloading of the waveforms over a protected Wi-Fi connection. Various Open Label SCS IPG implementations may be configured to increase battery life, increase charging capability, increase power of IPG, sense other physiologic parameters such as glucose, CBC, BMP, and triglycerides, and may be configured with an external battery which can be used when high power functions are needed such as vagal and extracranial stimulation.

An Open Label SCS IPG may be configured to permit customizing waveforms to work in together in a cycling or customizable manner. The disclosed Open Label SCS IPG design, implementation and usage techniques may be generalized to any medically implanted device which may benefit from electronic upgrading. Some Open Label SCS IPG implementations may be configured to monitor general body blood chemistry and heartrate. An Open Label SCS IPG may be configured to improve sleep by vagal stimulating effects or improve headache by transcranial application.

Although some exiting IPG designs have body position sensing ability, the IPG senses this information apriori; there is no wearable tech that provides information to the IPG or from the IPG to the wearables. Extracranial and vagal stimulators exist, but none connect with an SCS IPG to alter SCS function or are modified by an SCS IPG to minimize pain and mitigate tolerance.

In exemplary scenarios illustrative of prior art IPG design and usage, if a new waveform is suggested by a physician a patient has to undergo an explantation of a current IPG and re-implantation with a new device capable of running the recommended new waveform. Furthermore, implantation of the new device subjects the patient with the inability to run their older waveforms. Although current SCS IPG devices may be unlocked to allow for other waveforms to be uploaded to the devices, an exemplary Open Label SCS IPG may be configured to permit downloading/uploading waveforms from different companies onto other companies' currently implanted IPGs, or an implementation of the Open Label SCS IPG disclosed herein.

An exemplary SCS IPG method may comprise: receiving a digital indication comprising authorization to use at least two predetermined waveforms as input to an implantable pulse generator (IPG) configured for multiple waveform spinal cord stimulation (SCS), using a computing device operably coupled with the IPG; downloading and storing the at least two waveforms to the computing device and unlocking the IPG using code executing on the computing device to run the at least two waveforms on the IPG using an individualized alternating or cycling waveform protocol customized using the computing device; and using the individualized protocol with the IPG to limit physiologic tolerance to individual waveforms while stimulating a spinal cord. The method may further comprise customizing or editing SCS waveform signals to run on the IPG, using the computing device. The method may further comprise self-adjusting individualized protocols with different waveforms and stimulation patterns based on closed loop techniques using patient feedback, using the IPG.

An exemplary Open Label SCS IPG device may be configured for downloading and running multiple existing waveforms and using the waveforms to improve chronic pain syndromes. An exemplary Open Label SCS IPG may be capable of downloading predetermined waveforms. The waveforms may be run in individualized frequencies to maximize patient benefit. Various implementations may permit waveforms to be edited/created. An Open Label SCS IPG implementation may be configured to autonomously adjust waveforms using closed loop waveform adjustment algorithms. The Open Label SCS IPG may be configured to download pre-existing waveforms and run pre-existing waveforms in series or parallel to apply the waveforms using algorithmically determined waveform protocols. The waveform protocols may be algorithmically determined to cycle, alternate, or vary the waveforms to reduce pain syndrome tolerance to individual waveforms or waveform protocols. A feedback function assessing pain, sleep, and Heart Rate (HR) determined using sensor data may trigger a pre-programmed change in the waveform(s) protocol.

In the Summary above, in this Detailed Description, the Claims below, the content of each of the applications incorporated by reference herein and in the accompanying drawings, reference is made to features of various embodiments of the invention. It is to be understood that the disclosure of embodiments of the invention in this specification includes all possible combinations of such features. For example, where a particular feature is disclosed in the context of a particular aspect or embodiment of the invention, or a particular claim, that feature can also be used—to the extent possible—in combination with and/or in the context of other aspects and embodiments of the invention, and in the invention generally.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112(f), or 35 U.S.C. § 112, sixth paragraph (pre-AIA), unless the element is expressly recited using the phrase "means for" or "step for." These following claims should be construed to maintain the proper protection for the present invention.

What is claimed is:

1. A method comprising:
    configuring a universal spinal cord stimulator implantable pulse generator ("SCS IPG") (106) to measure at least one signal characteristic of at least one waveform protocol while the at least one waveform protocol is applied to a patient (115), using a SPS IPG processor (200);
    conducting a neuromodulation session in a pre-implant trial phase (148) using the SCS IPG (106), comprising the processor (200) and sensors (139), wherein the SCS IPG (106) is configured to run a plurality of waveform protocols (133) to treat the patient (115) with a pain syndrome (134), further wherein the pre-implant trial phase (148) comprises individually applying each of the plurality of waveform protocols (133) to the patient (115) in series to measure at least one corresponding physiological parameter (146) consisting of heart rate, heart rate variability and oxygen tension;
    storing the plurality of waveform protocols (133) and the at least one corresponding physiological parameter (146) in the SCS IPG (106) using the SCS IPG (106) processor (200);
    selecting a first waveform protocol (133) from the pre-implant trial phase (148) plurality of waveform protocols (133);
    implanting the SCS IPG (106) into the patient (115);
    applying the selected first waveform protocol (133) to the patient (115) during a treatment phase (151) to treat the pain syndrome (134) while measuring the at least one signal characteristic, using the SCS IPG processor (200);
    comparing the at least one signal characteristic measurement with known waveform protocols to determine if the selected first waveform protocol (133) matches any of the known waveform protocols, based on the comparison; and
    in response to determining the selected first waveform protocol (133) matches any known waveform protocol, sending to an authorization server (127) an indication the known waveform protocol is in use by the SCS IPG (106), using the SCS IPG (106) processor (200).

2. The method of claim 1, wherein the method further comprises determining if a physiologic tolerance of the pain syndrome (134) to the selected first waveform protocol changed as a function of comparing the at least one patient physiological parameter (146) measured during the treatment phase (151) to the same at least one patient physiological parameter (146) measured in the pre-implant trial phase (148) for the selected first waveform protocol, using the SCS IPG (106) processor (200).

3. The method of claim 2, wherein the method further comprises in response to determining the physiologic tolerance of the pain syndrome (134) changed during a feedback loop (143), initiating a modification of the first waveform protocol to an adapted waveform protocol (157), using the SCS IPG (106) processor (200).

4. The method of claim 3, wherein the method further comprises determining if the physiologic tolerance of the pain syndrome (134) to the adapted waveform protocol (157) changed as a function of comparing the at least one patient physiological parameter (146) measured in the feedback loop (143) to the same at least one patient physiological parameter (146) measured in a previous iteration of the feedback loop (143) for the same adapted waveform protocol (157), using the SCS IPG (106) processor (200).

5. The method of claim 4, wherein the method further comprises in response to determining the physiologic tolerance of the pain syndrome (134) to the adapted waveform protocol (157) changed during the feedback loop (143), initiating a modification of the adapted waveform protocol (157) using the SCS IPG (106) processor (200).

6. The method of claim 3, wherein the method further comprises:
    comparing the measured at least one signal characteristic of the adapted waveform protocol (157) with at least one signal characteristic of any known waveform protocols to determine if the adapted waveform protocol (157) matches at least one known waveform protocol, based on the comparison; and
    in response to determining the adapted waveform protocol (157) matches any known waveform protocols, sending to an authorization server (127) an indication the known waveform protocol is in use by the SCS IPG (106), using the SCS IPG (106) processor (200).

7. The method of claim 3, wherein the first waveform protocol or adapted waveform protocol comprises a licensed waveform.

8. The method of claim 7, wherein in response to sending the indication to the authorization server (127) that the known waveform protocol is in use by the SCS IPG (106), the method further comprises receiving a digital indication authorizing the SCS IPG (106) to use the licensed waveform, using the SCS IPG (106) processor (200).

9. The method of claim 1, wherein the at least one patient physiological parameter (146) further consists of RR interval (RR), and body temperature (TEMP).

10. The method of claim 1, wherein the at least one signal characteristic is one or more of: amplitude, frequency or duty cycle, wherein the signal characteristics are measured using the SCS IPG (106) processor (200).

11. The method of claim 1, wherein the neuromodulation session in the pre-implant trial phase (148) further comprises:
    applying each tested waveform protocol (133) for an active application time period and ceasing the application of each tested waveform protocol (133) for an inactive application time period;
    storing a time series of samples of the physiological parameters (146), sampled during the active application time period;
    storing a time series of samples of the physiological parameters (146), sampled during the inactive application time period; and
    establishing a reference pain syndrome tolerance to the tested waveform protocol (133) as a function of a comparison between the active application time series samples and the inactive application time series samples.

12. The method of claim 1, wherein determining if the selected first waveform protocol applied to the patient (115) matches any known waveform protocols further comprises determining a power spectrum correlation between the selected first waveform protocol and any known waveform protocol, using the SCS IPG (106) processor (200).

13. The method of claim 12, wherein the method further comprises determining the selected first waveform protocol matches a known waveform protocol upon determining the power spectrum correlation has a correlation coefficient value of at least 0.75.

14. The method of claim 1, wherein measuring the at least one signal characteristic comprises frequency domain sampling, using the SCS IPG (106) processor (200).

15. The method of claim 1, wherein configuring the SCS IPG (106) to measure at least one signal characteristic of at least one waveform protocol while the at least one waveform protocol is applied to the patient (115) further comprises configuring one or more energy output connection and one or more energy input connection with one or more electrodes, using the SCS IPG (106) processor (200).

16. A method comprising:
  configuring a universal spinal cord stimulator implantable pulse generator ("SCS IPG") (106) to measure at least one signal characteristic of at least one waveform protocol while the at least one waveform protocol is applied to a patient (115) having a pain syndrome (134), using an SPS IPG processor (200);
  applying a first selected waveform protocol (133) to the patient (115) during a treatment phase (151) using the SCS IPG implanted in the patient (115) to treat the pain syndrome (134) while measuring the at least one signal characteristic, using the SCS IPG processor (200);
  comparing the at least one signal characteristic measurement of the first selected waveform protocol (133) with known waveform protocols to determine if the selected first waveform protocol matches any of the known waveform protocols, based on the comparison; and
  in response to determining the selected first waveform protocol (133) matches any known waveform protocols, sending to an authorization server (127) an indication the known waveform protocol is in use by the SCS IPG (106), using the SCS IPG processor (200).

* * * * *